(12) United States Patent
Kula et al.

(10) Patent No.: US 6,242,234 B1
(45) Date of Patent: Jun. 5, 2001

(54) MUTANTS OF FORMATE DEHYDROGENASE FROM CANDIDA BOIDINII, NEW GENE SEQUENCES ENCODING THESE AND USE OF THE NEW FORMATE DEHYDROGENASES

(75) Inventors: Maria-Regina Kula, Niederzier; Martina Pohl, Aachen; Heike Slusarczyk, Ubach-Palenberg, all of (DE)

(73) Assignee: Degussa Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/203,893

(22) Filed: Dec. 2, 1998

(30) Foreign Application Priority Data

Dec. 3, 1997 (DE) .............................................. 197 53 350

(51) Int. Cl.[7] .............................. C12N 9/06; C12P 19/36; C12P 13/04; C12P 13/00
(52) U.S. Cl. ........................... 435/191; 435/90; 435/106; 435/128; 435/189; 435/440
(58) Field of Search .............................. 435/90, 128, 106, 435/189, 191, 440

(56) References Cited

PUBLICATIONS

Jour. B act., Jul. 1997, p. 4480–4485, Sakai, et al.

Sakai et al. (Jul. 1997) J. Bacteriology, vol. 179, pp. 4480–4485.*

Tishkov et al. (1993) BBRC, vol. 192(2), pp. 976–981.*

Allen et al. (1995) Gene, vol. 162, pp. 99–104.*

* cited by examiner

*Primary Examiner*—Elizabeth Slobodyansky
(74) *Attorney, Agent, or Firm*—Selitto, Behr & Kim

(57) ABSTRACT

The invention relates to new mutants of formate dehydrogenase from *Candida boidinii,* new gene sequences encoding these and use of the new formate dehydrogenases.

The wild type FDH used hitherto in the industrial process for preparing amino acids becomes inactive after a certain time. New mutants of this wild type have been produced by targeted mutagenesis of a recombinant FDH from *E. coli.* The new mutants are preferably used in an enzymatic process for preparing chiral compounds.

4 Claims, No Drawings

MUTANTS OF FORMATE DEHYDROGENASE FROM CANDIDA BOIDINII, NEW GENE SEQUENCES ENCODING THESE AND USE OF THE NEW FORMATE DEHYDROGENASES

FIELD OF THE INVENTION

The present invention relates to mutants of formate dehydrogenase from *Candida boidinii* (DSM 32195). The invention also relates to new gene sequences encoding these mutants and use of the formate dehydrogenases according to the invention in a process for preparing chiral compounds.

DISCUSSION OF THE PRIOR ART

To prepare L-amino acids, biocatalysts, inter alia, have been successfully used. One approach to the problem is to convert prochiral alpha-ketoacids by reductive amination. The amino acid dehydrogenases used for this purpose require stoichiometric amounts of NADH or NADPH as a coenzyme in order to convert the alpha-ketoacids. These coenzymes are very expensive and make the process mentioned above economically non-viable for use on an industrial scale.

One possibility of avoiding high costs due to the coenzyme comprises regenerating the coenzyme in situ. NAD-dependent formate dehydrogenase from the yeast *Candida boidinii* is currently used, inter alia, in the enzyme reactor for coenzyme regeneration on an industrial scale.

Reaction scheme 1

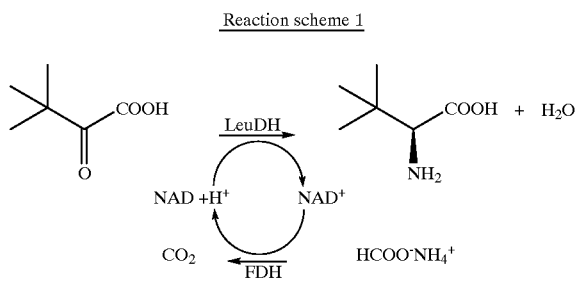

In situ regeneration of NADH with NAD-dependent formate dehydrogenase during the reductive amination of trimethyl pyruvate to give L-tert-leucine (Bommarius et al. Tetrahedron Asymmetry 1995, 6, 2851–2888).

A disadvantage of using FDH from *Candida boidinii* in a production process is the necessity of having to continue to add FDH during the process, since it becomes inactive as a result of lack of stability. This inactivation can be affected by a variety of factors:

pH
temperature
mechanical stress
ionic strength of and type of ion in the substrate solution
traces of heavy metals
oxidation of sulfhydryl groups by oxygen in the air
cross-linking due to thiol/disulfide exchange.

Tishkov et al. showed that targeted mutation of recombinant FDH from Pseudomonas sp. 101 could increase its stability towards mercury salts, whereas, however, the thermal stability was lowered by mutagenesis (Biochem, Biophys. Res. Commun. 1993, 192, 976–981).

Sakai et al. elucidated the gene sequence of FDH from the methylotrophic yeast *Candida boidinii* (J. Bacteriol. 1997, 179, 4480–4485). The protein sequence derived agreed 100% with the amino acid sequence of the basic recombinant FDH from *Candida boidinii* in this work.

SUMMARY OF THE INVENTION

In view of the prior art outlined and discussed above, it was also the object of the present invention to modify the FDH from *Candida boidinii* used in the industrial process in such a way that this has greater resistance to oxidation than recombinant FDH and the wild type and thus make costly and complicated post-addition of FDH during the process unnecessary.

Specifically, the invention is directed to stable mutants of rec-FDH from *Candida boidinii* having a higher level of stability to aggregation and oxidation than rec-FDH and the wild type enzyme. In these mutants one or more of the sulfur-containing amino acids in the rec-FDH are replaced by non sulfur containing amino acids. In particular those mutants wherein at least one of the cysteines at positions 23 and 262 is replaced by an amino acid selected from the group consisting of by serine, alanine or valine. The invention also includes the novel genes that encode these new mutants, in particular those genes, the DNA of which are set forth in sequences 1,3,5,7,9,11,13,15,17,19,21,23,25,27 and 29 hereof. The invention also includes the process of converting alpha keto acids into the corresponding chiral alpha amino acids in the presence of these mutants. Suitably this process is one wherein the conversion is carried out in the further presence of $NAD^+.H_2O$, preferably one wherein the conversion is carried out in the further presence of leucine dehydrogenase. Also included in the scope of the present invention is the process of preparing these mutant genes by means of targeted mutagenesis.

As a result of modifying the recombinant formate dehydrogenase from *Candida boidinii* by means of targeted mutagenesis, it has been possible in a very advantageous, and nevertheless surprising manner, to generate mutants which are not sensitive to aggregation and oxidation. These are unlike rec-FDH and the wild type enzyme, and thus to enable a longer working lifetime for this enzyme in a production process. Surprisingly, other advantageous properties of FDH, such as e.g. catalytic activity, conformational stability, thermal stability, etc. are only marginally affected so the new advantage is not negated by introducing different additional disadvantages. This could not have been predicted since, in such a complex molecule, even the smallest modification frequently leads to the complete loss of activity of the enzyme.

The recombinant formate dehydrogenase being considered is preferably modified in such a way that the sulfur-containing amino acids in the enzyme are replaced, independently, and separately or together, by amino acids which do not contain sulfur.

The cysteine units at positions 23 and 262 in FDH appear to be the particularly preferred targets of targeted mutation. Targeted mutagenesis may take place either at only one of these positions or at both. The sulfur-containing amino acids at positions 23 and/or 262 are advantageously replaced, independently, and separately or together, by amino acids without a sulfhydryl group. Replacement with serine, alanine or valine is particularly preferred.

The success of this modification, at the time when the invention was discovered, was neither predictable nor obvious, for the reasons given above.

The enzymes with improved stability encoded by the new gene sequences are preferably used in an enzymatic process for preparing chiral compounds, including the type mentioned at the beginning.

Enzymes with formate dehydrogenase activity according to the invention can advantageously be produced by means of targeted mutagenesis on the basis of the recombinant FDH gene and expressed in *E. coli*. Working with recombinant FDH offers the advantage that a standardised gene sequence and thus a standardised gene product is present, in which mutations can be produced. In order to be able effectively to compare the effects of the mutation in the mutants with the wild type enzyme, however, it is a critical advantage to be able to start from a standardised enzyme. There are probably several isoforms of the enzyme present in *Candida boidinii* itself and these are difficult to separate preparatively. In any case the wild enzyme exhibits microheterogeneities at the protein level.

In addition, all the advantages of *Escherichia coli* which are known to a person skilled in the art and relate to the parent organism, such as multiplication and expression, can be used.

DESCRIPTION OF THE PREFERRED EMBODIMENTS

The gene and amino acid sequences according to the invention can be prepared by biochemical and microbiological methods, which are known per se.

Thus, genomic DNA from *Candida boidinii* can be obtained by cultivation, lysis and precipitation using Ferbeyre et al.'s method (Bio Techniques 1993, 14. 386) The FDH gene can then be amplified by means of a polymerase chain reaction (PCR). The primers that were required were derived from protein sequence data. The FDH gene obtained was ligated in a cloning vector and transformed in *E. coli*. After isolating the recombinant plasmid DNA from the *E. coli* cells using a commercially available preparation kit (e.g. Qiagen Plasmid Tip 20), both DNA strands were sequenced. The sequence is shown in Sequences 31 and 32.

The recombinant plasmid DNA also acts as a template for PCR-promoted mutagenesis using Ho et al.'s method (Gene, 1989, 77, 52–59). The primers used contain the modified codon (in brackets) for replacement at the corresponding amino acid position: C23 (TGT bp 67–69) for S23 (TCT); C262 (TGT. bp 784–786) for V262 (GTT) or A262 (GCT). The amplified, mutated FDH genes were cloned in expression vector pBTac2 (Boehringer) (FIG. 2) and expressed in *E. coli*. The mutants were obtained from cells in the form of a crude cell-free extract by lysing the cultivated *E. coli*.

The advantage of the new enzymes is obvious from stability tests. The inactivation of recombinant FDH from *Candida boidinii*, of FDH-C23S, of FDH-C23S/C262A, of FDH-C23S/C262V and of FDH-C262V were measured in a comparative trial and their inactivation half-lives were determined. The results are given in Table 1.

TABLE 1

| Enzyme | Half-life (h) |
| --- | --- |
| recFDH | <21 |
| FDH-C23S/C262A | >750 |
| FDH-C23S | >750 |
| FDH-C23S/C262V | 160 |
| FDH-C262V | 21 |

The improvement in stability is obvious from the increase in half-lives of the mutants FDH-C23S/C262A, FDH-C23S and FDH-C23S/C262V. The notation FDH-C23S means that, in the formate dehydrogenase being considered, cysteine (C) has been replaced by serine (S) at position 23 in the protein sequence. In the same way, the expression FDH-C262V is understood to indicate that cysteine at position 262 has been replaced by valine.

The expression rec-FDH is understood to represent the recombinant formate dehydrogenase which can be obtained by cloning and expressing the gene from *Candida boidinii* in *E. coli* in accordance with the description given below.

Heterogeneous FDH, which can be obtained from *Candida boidinii*, is called the wild type enzyme.

The mutations of the present invention are set forth in detail in the sequences attached to this application and made part thereof. They can be summarised as follows.

TABLE 2

| Abbreviated name | DNA at codon 23 | Seq # | DNA at codon 262 | Seq # | Amino Acid at codon 23 | Seq # | Amino Acid at codon 262 | Seq # |
| --- | --- | --- | --- | --- | --- | --- | --- | --- |
| Rec-FDH | TGT | 31 | TGT | 31 | Cys | 32 | Cys | 32 |
| C23s | TCT | 1 | TGT | 1 | Ser | 1,2 | Cys | 1,2 |
| C23v | GTT | 3 | TGT | 3 | Val | 3,4 | Cys | 3,4 |
| C23a | GCT | 5 | TGT | 5 | Ala | 5,6 | Cys | 5,6 |
| C262s | TGT | 7 | TCT | 7 | Cys | 7,8 | Ser | 7,8 |
| C262v | TGT | 9 | GTT | 9 | Cys | 9,10 | Val | 9,10 |
| C262a | TGT | 11 | GCT | 11 | Cys | 11,12 | Ala | 11,12 |
| C23s/c262s | TCT | 13 | TCT | 13 | Ser | 13,14 | Ser | 13,14 |
| C23s/c262a | TCT | 15 | GCT | 15 | Ser | 15,16 | Ala | 15,16 |
| C23s/c262v | TCT | 17 | GTT | 17 | Ser | 17,18 | Val | 17,18 |
| C23a/c262s | GCT | 19 | TCT | 19 | Ala | 19,20 | Ser | 19,20 |
| C23a/c262a | GCT | 21 | GCT | 21 | Ala | 21,22 | Ala | 21,22 |
| C23a/c262v | GCT | 23 | GTT | 23 | Ala | 23,24 | Val | 23,24 |
| C23v/c262v | GTT | 25 | GTT | 25 | Val | 25,26 | Val | 25,26 |
| C23v/c262a | GTT | 27 | CGT | 27 | Val | 27,28 | Ala | 27,28 |
| C23v/c262s | GTT | 29 | TCT | 29 | Val | 29,30 | Ser | 29,30 |

The DNAs at the above codons are illustrative not limiting. The degenerated base triplets encoding the same amino acids are within the scope of this invention. The following examples are intended to illustrate the invention.

EXAMPLES

Example 1

Preparing Genomic DNA from *Candida boidinii*

Preparing genomic DNA from the yeast was performed using a modified form of Ferbeyre et al.'s method (Bio Techniques 1993, 14, 386). The *Candida boidinii* cells were cultivated in 200 ml of YEPD medium at 30° C. and 200 rpm up to the time of the late logarithmic growth phase and then harvested by centrifuging (10 min, 15° C., 5000 rpm, GSA rotor). Under these conditions, about 2.0 g of moist cell material were produced per 100 ml of culture. The cells were washed once with 10 mM citrate phosphate buffer, pH 7.5, and then resuspended in 10 ml of lysis buffer. 1 mg of protease [Qiagen] and 200 units of lyticase from *Arthrobacter luteus* [Sigma] per ml of lysis buffer were added to the cell suspension. The suspension was incubated for 60 min at 37° C. and then extracted with the same volume (vol.) of phenol/chloroform/isoamyl alcohol (PCI). After centrifuging for 30 min at RT and 12000 rpm in a SS34 rotor, the aqueous phase was removed and again extracted with PCI when a large interphase appeared. The DNA was then precipitated in the aqueous phase with 1/10 vol. of 3 M sodium acetate, pH 5.2, and 2 vol. of ice-cold ethanol (abs.), placed on ice for 5 min, wound onto a glass rod and dried under the sterile bank. After drying, the DNA was dissolved overnight in 5 ml of TE, pH 7.5, at 4° C. The RNA in the DNA preparation was digested by adding 100 µg of RNAse'A per ml of solution and incubating for 60 min at 37° C. with slight shaking on a horizontal shaker (40 rpm). Then the RNAseA was precipitated by extracting with one vol. of PCI and the aqueous phase was extracted once with one vol. of CI in order to remove traces of phenol. After centrifuging, the DNA was precipitated from the aqueous phase at RT using 1/10 vol. of 3M sodium acetate, pH 5.2, and 0.7 vol. of 2-propanol. wound onto a glass rod and dried in the same way as before. The genomic DNA (gDNA) was dissolved overnight in 2:5 ml of TE, pH 7.5 at 4° C.

The size distribution of the gDNA was then analysed in a 0.5% strength agarose gel and quantified and qualified by determining the OD260nm and OD280nm.

High molecular weight DNA which was clean enough for most microbiological applications could be obtained in good yield (700 pg of genomic DNA per g of moist cell material) using this method.

| Composition of the media and buffers used: | |
|---|---|
| YEPD medium: | 1% (w/v) yeast extract |
| | 2% (w/v) peptone |
| | 2% (w/v) glucose |
| Lysis buffer: | 10 mM citrate phosphate pH 7.5 |
| | 1 M sorbitol |
| | 100 mM EDTA |
| | 1% (w/v) SDS |
| | 1% (v/v) β-mercaptoethanol |
| TE pH 7.5: | 10 mM Tris-HCl, pH 7.5 |
| | 1 mM EDTA |
| PCI | phenol/chloroform/isoamyl/alcohol (25:24:1) |
| CI | chloroform/isoamyl alcohol (24:1) |

Example 2

Amplifying the FDH Gene Using PCR Starting from Genomic DNA

All PCR batches were covered with a layer of 50–100 µl of light mineral oil [Sigma] and PCR was performed using an automatic DNA thermal cycler [Robocycler, Stratagene] in accordance with the following programme:

PCR programme:
  2 min. denaturation at 94° C. (1 x at start of programme)
  1 min denaturation at 94° C.
  1.5 min. annealing of primer at 46–60° C. (depending on the melting point of the primer)
  1.5 min. extension at 72° C. (to extend primer by means of Taq polymerase) cyclic repetition of last three steps (25–30 x)
  10 min. extension at 72° C. to ensure that all the amplified fragments are fully extended.
The PCR mixture contains.
  100 ng of gDNA
  20 pmol of primer N-TermF3
  20 pmol of primer C-TermR5
  0.2 mM each of dNTPs
  0.5 µl of Taq polymerase (Boehringer)
  10 µl of buffer 10x (Boehringer)
  ad 100 µl with dist. water
  Annealing temperature: 48° C., 35 cycles
The PCR fragment was ligated using Sure Clone kits (Pharmacia, Freiburg) in the vector pUC18. Hanahan's method (J. Mol. Biol. 1983, 166, 557) was used for transformation. 2 µl of ligation mixture vector pUC-FDH were added to 100 µl of competent *E coli* XL1 blue cells.

Example 3

Preparing Mutants FDH-C23S

The point mutants of FDH were produced on the basis of the cloned FDH gene (pUC-FDH) (see example 1) using Ho et al.'s method (Gene 1989, 77, 52–59). The following "internal" oligonucleotide primers, which contained both the mutations, were used:
  internal primer for introducing C23S mutation:
  S23sense, 5'-TTTTCAGTAGMCCATATAA-3' (SEQ ID NO:33)
  S23antisense: 5'-TATATGGTTCTACTGAAAAT-3' (SEQ ID NO:34)
The following oligonucleotide primers were used as "external" primers:
  PUC181S: 5'-CGCGCGTTTCGGTGATGACG-3' (SEQ ID NO:35)
  C-TermR5/Pstl:
    5'-CTGCAGTTATTTCTTATCGTGTTTACCGTA-3' (SEQ ID NO:36)
  N-TermF3IEcoR1:
    5'-GAATTCATGAAGATTGTCTTAGTTCTTTAT-3' (SEQ ID NO:37)
1. Preparation of individual fragments:
  Mixture A: Preparing SER23S1-CTERMR5/Pstl —fragments (1.0 kb)
    100 ng pUC-FDH (1.1 kbFDH-EcoRl/Pstl in pUC18)
    30 pmol of primer SER23SI
    30 pmol of primer CTERMR5/Pstl
    1.5 µl of Pfu-polymerase (2.5 U/µl)
    1/10 vol polymerase buffer 10x
    0.2 mM each of dNTP
    ad 100 µl with dist. water
    Annealing temperature: 46° C., 30 cycles
  Mixture B: Preparing PUC18SI-SER23AS1 -fragments (500 bp)
    100 ng of pUC-FDH (see above)
    30 pmol of primer PUC 18SI 30 pmol of primer SER23ASI
1.5 1 µl of Pfu-polymerase (see above)
1/10 vol of poiymerase buffer 10x
0.2 mM each of dNTP
ad 100 µl with dist. water
Annealing temperature: 44° C., 30 cycles.

After the PCR programme, the mixtures were separated in a preparative agarose gel (1%), the bands were cut out, isolated by using Jetsorb gel extraction kits (Genomed), the concentrations were estimated in an analytical agarose gel (reference material: 1 µg of kb-ladder, Gibco) and used as a template in fusion PCR with overlapping fragments.

2. Fusion PCR for preparing the complete FDH-C23S gene (1.1 kb)
150 ng of SER23S1-CTERMR5/PstI fragment
90 ng of PUC18SI -SER23ASI fragment
20 pmol pfimer NTERMF3/EcoRl
20 pmol of primer CTERMR5/PstI
1.5 µl of Pfu-polymerase (2.5 U/µl)
1/10 vol of polymerase buffer 10x
0.2 mM each of dNTP
ad 100 µl with dist. water
Annealing-T.: 46° C. 30 cycles The PCR mixture was used directly in A-tailing (see below).

3. Cloning the PCR products in pMOS blue:
Cloning was performed with pMOS blue T-vector kits (Amersham)
a) A-tailing
100 µl of fusion PCR mixture were extracted with 1 vol of chloroform/isoamyl alcohol (Cl) (24:1).
25 µl of aqueous phase=¼ of the PCR mixture
1.8 µl 10 x buffer (see Amersham instruction sheet)
1.8 µl dNTP-Mix (see Amersham instruction sheet)
8.5 µl A-tailing buffer (see Amersham instruction sheet)
0.5 µl of Tth-DNA-polymerase
ad 85 µl with dist. water
15 min at 70° C.
extracted 1 x with Cl After isolating the PCR fragment containing the FDH-C23S gene by agarose gel electrophoresis and isolation of the PCR fragment using Jet-Sorb (Genomed), the fragment was ligated in the vector pMOS blue.

Ligation in pMOS blue:
50 ng of pMOS blue vecto
120 ng of FDH-Ser23 - 3'dA
0.5 µl of ATP 10 mM
1.0 µl of ligase buffer
0.5 µl DTT 100 mM
0.5 µl of T4 DNA ligase (2–3 Weiss Units)
ad 10 µl with dist. water
Incubation overnight at 16° C.

b) Transformation in MOS blue competent cells (according to Amersham Instructions, 1994)
1 µl of ligation mixture
20 µl of competent cells
40 sec 42° C.
2 min on ice
80 µl of LB medium added, 1 h 37° C.
50 µl plated out on LB with ampicillin and tetracyclin.

4. Cloning the FDH-C23S gene in the expression vector PBTac2 (Boehringer)

The plasmid DNA (pMOS-FDH-C23S) was isolated from the recombinant pMOS blue cells after multiplication in *E. coli* and the FDH-C23S-EcoRl/PstI fragment (1.1 kb) was prepared by means of restriction digestion.

Preparative EcoRl-PstI digestion
15 µl of plasmid DNA (ca. 200 ng) pMOS-FDH-C23S
3 µl of buffer H (Boehringer)
0.5 µl of EcoRl (10U/µl)
0.5 µl of PstI (10U/µl)
11 µl dist. water.
2 h, 37° C.

The fragment was isolated using the method mentioned above.

Ligation in pBTac2
100 ng of pBTac2 were digested, as described above, with EcoRl and PstI, and the linearised vector was isolated using the method mentioned above. The FDH-C23S-EcoRl /PstI fragment (1.1 kb) was ligated in the open vector.

The ligation mixture contained:
45 ng of pBTac2-EcoRl/PstI
60 ng of FDH-C23S-EcoRl/PstI
1 µl of ligase buffer 10x (Boehringer)
0.5 µl of T4 DNA ligase (Boehringer)
ad 10 µl with dist. water
Incubated overnight at 16° C.

5. Transformation in *E. coli* JM 105
For the transformation, 100 µl of competent *E. coli* JM 105 cells were added to 5 µl of ligation mixture and transformation was performed using Hanahan's method (see above).

Example 4

Expression of FDH-C23S in *E. coli*

The recombinant wild type FDH gene and the FDH mutants were expressed on a 200 ml scale in *E. coli* JM1 05 cells. 200 ml of LB medium were added to select 100 µg of ampicillin per ml and inoculated in the ratio of 1:50 with a preliminary culture which had been incubated overnight. The cells were cultivated at 37° C. and 180 rpm on a reciprocating shaker and induced with 1 mM of IPTG at an optical density (OD 550 nm) of 0.6–0.8. The expression time was between 5.0 h (0.7 g of moist cell material) and 20 h (1.25 g of moist cell material). The cells were harvested by centrifuging (10 min, GSA rotor, 10,000 rpm).

| | |
|---|---|
| LB (Luria Bertani) medium: | 1.0% Bacto - Tryptone |
| | 0.5% Bacto - yeast extract |
| | 1.0% NaCl adjusted to pH 7.5 with NaOH |
| LBamp medium | LB medium with 100 µg/ml ampicillin |

Cell lysis took place mechanically using glass beads (diameter 0.3 mm). A 30% strength *E. coli* cell suspension was prepared in the lysis buffer, to which was added twice the weight of glass beads. Lysis took place, depending on the volume, on a 1–2 ml scale in a vibratory mill [Retsch; Hummel and Kula (1989) J. Microbiol. Meth. 9, 210], in a SS34 centrifuge tube (10–20 ml), in a vortex [IKA] or in a disintegrator S (20–50 ml) [IMA] for a period of 20 min. The lysed product was centrifuged for 10 min at 10000 rpm and 4° C., the cell-free supernatant liquid was removed and the glass beads and cell pellets were washed once with a volume of buffer equal to ¼–½ the volume of cell suspension. After centrifuging a second time, the cell-free supernatant liquids were combined. The volume activity of the FDH-C23S in the crude cell-free extract was 10 U/ml

| | |
|---|---|
| Lysis buffer: | 100 mM of potassium phosphate buffer, pH 7.5 |
| | 10 drops of Ucolup/L buffer |

Example 5

Determining the Stability of the FDH-C23S

The crude cell-free extract of FDH-C23S was used to determine the half-life for deactivation.

The test mixtures contained: 0.05–0.5 M $NH_4$-trimethyl pyruvate 0.1–1 M L-tert. leucine 2.7 M $NH_4$-formate 0.5 U/ml FDH-C23S pH 6–9

T=40° C.

The mixtures were incubated for 18 days. Samples for activity tests were taken each day. The semi-logarithmic plot of residual activity against time was a straight line, whose gradient gave the inactivation constant k. The half-life □ for inactivation was obtained from the relationship □=ln2/k.

Example 6

Synthesis of (S)-neopentylglycine 31.53g (0.5 mole) ammonium formate and 20.89 g (125 mmole), 2~-keto-4,4~dimethyl-pentanoic acid sodium salt are suspended in 400 ml of water, the pH value is adjusted with ammonia to pH 8.5 to provide a solution, the volume is adjusted then to 500 ml. Subsequently, 71.7 mg (0.1 mmole) $NAD^+ H_2O$ cofactor as well as 2000 U of leucine dehydrogenase (LeUDH) and 2500 U of rec-formate dehydrogenase (rec-FDH) are added. The temperature is set to 28° C. The reaction is gently stirred and the pH value is adjusted to 8.2 during the reaction by a pH stat unit. The completion point of the reaction is demonstrated by determining the degree of conversion with HPLC. The enzymes are separated via an ultra filter of pore size 10000 kDA and the solution is adjusted with ammonia to pH 9.5 subsequently, the solution is clarified with 2% active charcoal and the almost colourless solution is concentrated with a rotary evaporator, the amino acid is crystallized, separated via a filter funnel, washed three times with small amounts of ethanol and dried overnight under vacuum at 50° C.

Example 7

Synthesis of (5)-3-methyl-isoleucine ((S)-3,3-dimethyl-norvalin)

6.3 g (0.1 mole) ammonium formate and 1.67 g (10 mmoles), 2-keto-3,3-dimethyl pentanoic acid sodium salt are suspended in 80 ml of water, the pH value is adjusted with ammonia to 8.2, so that the solids dissolve and the volume is adjusted to 100 ml. subsequently, 14.34 mg (0.02 mmole) $NAD^+3H_2O$ cofactor as well as 800 U of leucine dehydrogenase (LeUDH) and 500 U of rec-formate dehydrogenase (rec-FDH) are added. The temperature is set to 32° C . During the reaction the system is gently stirred and the pH value is adjusted to 8.2 via a pH stat unit. The completion point of the reaction is sdemonstrated by determining the degree of conversion with HPLC. The reaction solution is adjusted to pH 9,5 with ammonia and subsequently clarified with 2% active charcoal. The almost colourless solution is concentrated with a rotary evaporator, the amino acid is crystallized, is separated via a filter funnel, washed three times with a little ethanol and dried overnight under vacuum at 50° C.

Example 8

Synthesis of (S) nornoneopentyiglycine ((S)-5,5-dimethyl norleucin)

Reaction and isolation are carried out analogously to example 7. Substrate charged: 1.81 g (10 mmole) of 2-keto-S,5-dimethyl-hexanoic acid sodium salt.

We claim:

1. Stable mutants of recombinant formate dehydrogenase (FDH) from *Candida boidinii* having a higher level of stability to aggregation and oxidation than recombinant FDH and the wild type enzyme, wherein one or more of the cysteines in the recombinant FDH are replaced by non-sulphur containing amino acids wherein at least the cysteine at position corresponding to position 23 in SEQ ID NO:32 is replaced by an amino acid selected from the group consisting of serine, alanine and valine.

2. A process of converting alpha keto acids by reaction with a NADPH or NADH dependent amino acid dehydrogenase in the presence of mutants according to claim 1, into the corresponding chiral alpha amino acids.

3. The process of claim 2 wherein the conversion is carried out in the further presence of $NAD^+ \cdot H_2O$.

4. The process of claim 2 wherein the dehydrogenase is leucine dehydrogenase.

* * * * *

SEQUENCE LISTING

```
<160> NUMBER OF SEQ ID NOS: 37

<210> SEQ ID NO: 1
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 1 atg aag att gtc tta gtt ctt tat gat gct ggt aag cac gct gct gat        48
Met Lys Ile Val Leu Val Leu Tyr Asp Ala Gly Lys His Ala Ala Asp
  1               5                  10                  15 gaa gaa aaa tta tat ggt tca act gaa aat aaa tta ggt att gcc aat        96
Glu Glu Lys Leu Tyr Gly Ser Thr Glu Asn Lys Leu Gly Ile Ala Asn
              20                  25                  30 tgg tta aaa gat caa ggt cat gaa cta att act act tct gat aaa gaa       144
Trp Leu Lys Asp Gln Gly His Glu Leu Ile Thr Thr Ser Asp Lys Glu
```

```
                35                    40                    45
ggt gaa aca agc gaa ttg gat aaa cat atc cca gat gct gat att atc        192
Gly Glu Thr Ser Glu Leu Asp Lys His Ile Pro Asp Ala Asp Ile Ile
         50                      55                      60 atc acc act cct ttc cat cct gct tat atc act aag gaa aga ctt gac        240
Ile Thr Thr Pro Phe His Pro Ala Tyr Ile Thr Lys Glu Arg Leu Asp
 65                      70                      75                  80 aag gct aag aac tta aaa tta gtc gtt gtc gct ggt gtt ggt tct gat        288
Lys Ala Lys Asn Leu Lys Leu Val Val Val Ala Gly Val Gly Ser Asp
                     85                      90                      95 cac att gat tta gat tat att aat caa aca ggt aag aaa atc tca gtc        336
His Ile Asp Leu Asp Tyr Ile Asn Gln Thr Gly Lys Lys Ile Ser Val
                    100                     105                     110 ctg gaa gtt aca ggt tct aat gtt gtc tct gtt gct gaa cac gtt gtc        384
Leu Glu Val Thr Gly Ser Asn Val Val Ser Val Ala Glu His Val Val
                115                     120                     125 atg acc atg ctt gtc ttg gtt aga aat ttc gtt cca gca cat gaa caa        432
Met Thr Met Leu Val Leu Val Arg Asn Phe Val Pro Ala His Glu Gln
130                     135                     140 att att aac cac gat tgg gag gtt gct gct atc gct aag gat gct tac        480
Ile Ile Asn His Asp Trp Glu Val Ala Ala Ile Ala Lys Asp Ala Tyr
145                     150                     155                 160 gat atc gaa ggt aaa act atc gct acc att ggt gct ggt aga att ggt        528
Asp Ile Glu Gly Lys Thr Ile Ala Thr Ile Gly Ala Gly Arg Ile Gly
                    165                     170                     175 tac aga gtc ttg gaa aga tta ctc cca ttt aat cca aaa gaa tta tta        576
Tyr Arg Val Leu Glu Arg Leu Leu Pro Phe Asn Pro Lys Glu Leu Leu
                180                     185                     190 tac tac gat tat caa gct tta cca aaa gaa gct gaa gaa aaa gtt ggt        624
Tyr Tyr Asp Tyr Gln Ala Leu Pro Lys Glu Ala Glu Glu Lys Val Gly
            195                     200                     205 gct aga aga gtt gaa aat att gaa gaa tta gtt gct caa gct gat atc        672
Ala Arg Arg Val Glu Asn Ile Glu Glu Leu Val Ala Gln Ala Asp Ile
        210                     215                     220 gtt aca gtt aat gct cca tta cac gca ggt aca aaa ggt tta att aat        720
Val Thr Val Asn Ala Pro Leu His Ala Gly Thr Lys Gly Leu Ile Asn
225                     230                     235                 240 aag gaa tta tta tct aaa ttt aaa aaa ggt gct tgg tta gtc aat acc        768
Lys Glu Leu Leu Ser Lys Phe Lys Lys Gly Ala Trp Leu Val Asn Thr
                    245                     250                     255 gca aga ggt gct att tgt gtt gct gaa gat gtt gca gca gct tta gaa        816
Ala Arg Gly Ala Ile Cys Val Ala Glu Asp Val Ala Ala Ala Leu Glu
                260                     265                     270 tct ggt caa tta aga ggt tac ggt ggt gat gtt tgg ttc cca caa cca        864
Ser Gly Gln Leu Arg Gly Tyr Gly Gly Asp Val Trp Phe Pro Gln Pro
            275                     280                     285 gct cca aag gat cac cca tgg aga gat atg aga aat aaa tat ggt gct        912
Ala Pro Lys Asp His Pro Trp Arg Asp Met Arg Asn Lys Tyr Gly Ala
        290                     295                     300 ggt aat gcc atg act cct cac tac tct ggt act act tta gac gct caa        960
Gly Asn Ala Met Thr Pro His Tyr Ser Gly Thr Thr Leu Asp Ala Gln
305                     310                     315                 320 aca aga tac gct gaa ggt act aaa aat att ttg gaa tca ttc ttt acc       1008
Thr Arg Tyr Ala Glu Gly Thr Lys Asn Ile Leu Glu Ser Phe Phe Thr
                    325                     330                     335 ggt aaa ttt gat tac aga cca caa gat att atc tta tta aat ggg gaa       1056
Gly Lys Phe Asp Tyr Arg Pro Gln Asp Ile Ile Leu Leu Asn Gly Glu
                340                     345                     350 tac gtt act aaa gct tac ggt aaa cac gat aag aaa tag                   1095
```

```
Tyr Val Thr Lys Ala Tyr Gly Lys His Asp Lys Lys
        355             360

<210> SEQ ID NO: 2
<211> LENGTH: 364
<212> TYPE: PRT
<213> ORGANISM: Candida boidinii

<400> SEQUENCE: 2

Met Lys Ile Val Leu Val Leu Tyr Asp Ala Gly Lys His Ala Ala Asp
 1               5                  10                  15

Glu Glu Lys Leu Tyr Gly Ser Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
 50                  55                  60

Ile Thr Thr Pro Phe His Pro Ala Tyr Ile Thr Lys Glu Arg Leu Asp
 65                  70                  75                  80

Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
                100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
                180                 185                 190

Tyr Tyr Asp Tyr Gln Ala Leu Pro Lys Glu Ala Glu Lys Val Gly
            195                 200                 205

Ala Arg Arg Val Glu Asn Ile Glu Glu Leu Val Ala Gln Ala Asp Ile
210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Leu Glu
                260                 265                 270

Ser Gly Gln Leu Arg Gly Tyr Gly Gly Asp Val Trp Phe Pro Gln Pro
            275                 280                 285

Ala Pro Lys Asp His Pro Trp Arg Asp Met Arg Asn Lys Tyr Gly Ala
290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355             360
```

```
<210> SEQ ID NO: 3
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 3 atg aag att gtc tta gtt ctt tat gat gct ggt aag cac gct gct gat      48
Met Lys Ile Val Leu Val Leu Tyr Asp Ala Gly Lys His Ala Ala Asp
 1               5                  10                  15 gaa gaa aaa tta tat ggt gtc act gaa aat aaa tta ggt att gcc aat      96
Glu Glu Lys Leu Tyr Gly Val Thr Glu Asn Lys Leu Gly Ile Ala Asn
                20                  25                  30 tgg tta aaa gat caa ggt cat gaa cta att act act tct gat aaa gaa     144
Trp Leu Lys Asp Gln Gly His Glu Leu Ile Thr Thr Ser Asp Lys Glu
            35                  40                  45 ggt gaa aca agc gaa ttg gat aaa cat atc cca gat gct gat att atc     192
Gly Glu Thr Ser Glu Leu Asp Lys His Ile Pro Asp Ala Asp Ile Ile
        50                  55                  60 atc acc act cct ttc cat cct gct tat atc act aag gaa aga ctt gac     240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat     288
Lys Ala Lys Asn Leu Lys Leu Val Val Val Ala Gly Val Gly Ser Asp
                85                  90                  95 cac att gat tta gat tat att aat caa aca ggt aag aaa atc tca gtc     336
His Ile Asp Leu Asp Tyr Ile Asn Gln Thr Gly Lys Lys Ile Ser Val
                100                 105                 110 ctg gaa gtt aca ggt tct aat gtt gtc tct gtt gct gaa cac gtt gtc     384
Leu Glu Val Thr Gly Ser Asn Val Val Ser Val Ala Glu His Val Val
            115                 120                 125 atg acc atg ctt gtc ttg gtt aga aat ttc gtt cca gca cat gaa caa     432
Met Thr Met Leu Val Leu Val Arg Asn Phe Val Pro Ala His Glu Gln
        130                 135                 140 att att aac cac gat tgg gag gtt gct gct atc gct aag gat gct tac     480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt     528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta     576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt     624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc     672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat     720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc     768
Lys Glu Leu Leu Ser Lys Phe Lys Lys Gly Ala Trp Leu Val Asn Thr
                245                 250                 255 gca aga ggt gct att tgt gtt gct gaa gat gtt gca gca gct tta gaa     816
Ala Arg Gly Ala Ile Cys Val Ala Glu Asp Val Ala Ala Ala Leu Glu
            260                 265                 270
```

```
tct ggt caa tta aga ggt tac ggt ggt gat gtt tgg ttc cca caa cca      864
Ser Gly Gln Leu Arg Gly Tyr Gly Gly Asp Val Trp Phe Pro Gln Pro
            275                 280                 285 gct cca aag gat cac cca tgg aga gat atg aga aat aaa tat ggt gct      912
Ala Pro Lys Asp His Pro Trp Arg Asp Met Arg Asn Lys Tyr Gly Ala
        290                 295                 300 ggt aat gcc atg act cct cac tac tct ggt act act tta gac gct caa      960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc     1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa     1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag                  1095
Tyr Val Thr Lys Ala Tyr Gly Lys His Asp Lys Lys
                355                 360

<210> SEQ ID NO: 4
<211> LENGTH: 364
<212> TYPE: PRT
<213> ORGANISM: Candida boidinii

<400> SEQUENCE: 4
```

Met Lys Ile Val Leu Val Leu Tyr Asp Ala Gly Lys His Ala Ala Asp
1               5                   10                  15

Glu Glu Lys Leu Tyr Gly Val Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
        50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr

-continued

```
                    245                 250                 255
Ala Arg Gly Ala Ile Cys Val Ala Glu Asp Val Ala Ala Leu Glu
            260                 265                 270

Ser Gly Gln Leu Arg Gly Tyr Gly Asp Val Trp Phe Pro Gln Pro
            275                 280             285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360

<210> SEQ ID NO: 5
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 5 atg aag att gtc tta gtt ctt tat gat gct ggt aag cac gct gct gat      48
Met Lys Ile Val Leu Val Leu Tyr Asp Ala Gly Lys His Ala Ala Asp
  1               5                  10                  15 gaa gaa aaa tta tat ggt gct act gaa aat aaa tta ggt att gcc aat      96
Glu Glu Lys Leu Tyr Gly Ala Thr Glu Asn Lys Leu Gly Ile Ala Asn
                 20                  25                  30 tgg tta aaa gat caa ggt cat gaa cta att act act tct gat aaa gaa     144
Trp Leu Lys Asp Gln Gly His Glu Leu Ile Thr Thr Ser Asp Lys Glu
             35                  40                  45 ggt gaa aca agc gaa ttg gat aaa cat atc cca gat gct gat att atc     192
Gly Glu Thr Ser Glu Leu Asp Lys His Ile Pro Asp Ala Asp Ile Ile
         50                  55                  60 atc acc act cct ttc cat cct gct tat atc act aag gaa aga ctt gac     240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat     288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc     336
His Ile Asp Leu Asp Tyr Ile Asn Gln Thr Gly Lys Lys Ile Ser Val
                100                 105                 110 ctg gaa gtt aca ggt tct aat gtt gtc tct gtt gct gaa cac gtt gtc     384
Leu Glu Val Thr Gly Ser Asn Val Val Ser Val Ala Glu His Val Val
            115                 120                 125 atg acc atg ctt gtc ttg gtt aga aat ttc gtt cca gca cat gaa caa     432
Met Thr Met Leu Val Leu Val Arg Asn Phe Val Pro Ala His Glu Gln
        130                 135                 140 att att aac cac gat tgg gag gtt gct gct atc gct aag gat gct tac     480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt     528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta     576
```

```
                                                                         -continued Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt     624
Tyr Tyr Asp Tyr Gln Ala Leu Pro Lys Glu Ala Glu Glu Lys Val Gly
                195                 200                 205 gct aga aga gtt gaa aat att gaa gaa tta gtt gct caa gct gat atc     672
Ala Arg Arg Val Glu Asn Ile Glu Glu Leu Val Ala Gln Ala Asp Ile
        210                 215                 220 gtt aca gtt aat gct cca tta cac gca ggt aca aaa ggt tta att aat     720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc     768
Lys Glu Leu Leu Ser Lys Phe Lys Lys Gly Ala Trp Leu Val Asn Thr
                245                 250                 255 gca aga ggt gct att tgt gtt gct gaa gat gtt gca gca gct tta gaa     816
Ala Arg Gly Ala Ile Cys Val Ala Glu Asp Val Ala Ala Ala Leu Glu
        260                 265                 270 tct ggt caa tta aga ggt tac ggt ggt gat gtt tgg ttc cca caa cca     864
Ser Gly Gln Leu Arg Gly Tyr Gly Gly Asp Val Trp Phe Pro Gln Pro
                275                 280                 285 gct cca aag gat cac cca tgg aga gat atg aga aat aaa tat ggt gct     912
Ala Pro Lys Asp His Pro Trp Arg Asp Met Arg Asn Lys Tyr Gly Ala
        290                 295                 300 ggt aat gcc atg act cct cac tac tct ggt act act tta gac gct caa     960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc    1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa    1056
Gly Lys Phe Asp Tyr Arg Pro Gln Asp Ile Ile Leu Leu Asn Gly Glu
        340                 345                 350 tac gtt act aaa gct tac ggt aaa cac gat aag aaa tag                1095
Tyr Val Thr Lys Ala Tyr Gly Lys His Asp Lys Lys
                355                 360

<210> SEQ ID NO: 6
<211> LENGTH: 364
<212> TYPE: PRT
<213> ORGANISM: Candida boidinii

<400> SEQUENCE: 6

Met Lys Ile Val Leu Val Leu Tyr Asp Ala Gly Lys His Ala Ala Asp
 1               5                  10                  15

Glu Glu Lys Leu Tyr Gly Ala Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125
```

```
Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
                260                 265                 270

Ser Gly Gln Leu Arg Gly Tyr Gly Gly Asp Val Trp Phe Pro Gln Pro
    275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
                340                 345                 350

Tyr Val Thr Lys Ala Tyr Gly Lys His Asp Lys Lys
                355                 360

<210> SEQ ID NO: 7
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 7 atg aag att gtc tta gtt ctt tat gat gct ggt aag cac gct gct gat    48
Met Lys Ile Val Leu Val Leu Tyr Asp Ala Gly Lys His Ala Ala Asp
  1               5                  10                  15 gaa gaa aaa tta tat ggt tgt act gaa aat aaa tta ggt att gcc aat    96
Glu Glu Lys Leu Tyr Gly Cys Thr Glu Asn Lys Leu Gly Ile Ala Asn
             20                  25                  30 tgg tta aaa gat caa ggt cat gaa cta att act act tct gat aaa gaa   144
Trp Leu Lys Asp Gln Gly His Glu Leu Ile Thr Thr Ser Asp Lys Glu
         35                  40                  45 ggt gaa aca agc gaa ttg gat aaa cat atc cca gat gct gat att atc   192
Gly Glu Thr Ser Glu Leu Asp Lys His Ile Pro Asp Ala Asp Ile Ile
     50                  55                  60 atc acc act cct ttc cat cct gct tat atc act aag gaa aga ctt gac   240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat   288
Lys Ala Lys Asn Leu Lys Leu Val Val Val Ala Gly Val Gly Ser Asp
                 85                  90                  95
```

```
cac att gat tta gat tat att aat caa aca ggt aag aaa atc tca gtc    336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc    384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa    432
Met Thr Met Leu Val Leu Val Arg Asn Phe Val Pro Ala His Glu Gln
130                 135                 140 att att aac cac gat tgg gag gtt gct gct atc gct aag gat gct tac    480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt    528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta    576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt    624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc    672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat    720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc    768
Lys Glu Leu Leu Ser Lys Phe Lys Lys Gly Ala Trp Leu Val Asn Thr
                245                 250                 255 gca aga ggt gct att tct gtt gct gaa gat gtt gca gca gct tta gaa    816
Ala Arg Gly Ala Ile Ser Val Ala Glu Asp Val Ala Ala Ala Leu Glu
            260                 265                 270 tct ggt caa tta aga ggt tac ggt ggt gat gtt tgg ttc cca caa cca    864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct    912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa    960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc   1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa   1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag               1095
Tyr Val Thr Lys Ala Tyr Gly Lys His Asp Lys Lys
        355                 360

<210> SEQ ID NO: 8
<211> LENGTH: 364
<212> TYPE: PRT
<213> ORGANISM: Candida boidinii

<400> SEQUENCE: 8

Met Lys Ile Val Leu Val Leu Tyr Asp Ala Gly Lys His Ala Ala Asp
  1               5                  10                  15
```

```
Glu Glu Lys Leu Tyr Gly Cys Thr Glu Asn Lys Leu Gly Ile Ala Asn
             20                  25                  30
Trp Leu Lys Asp Gln Gly His Glu Leu Ile Thr Thr Ser Asp Lys Glu
         35                  40                  45
Gly Glu Thr Ser Glu Leu Asp Lys His Ile Pro Asp Ala Asp Ile Ile
     50                  55                  60
Ile Thr Thr Pro Phe His Pro Ala Tyr Ile Thr Lys Glu Arg Leu Asp
 65                  70                  75                  80
Lys Ala Lys Asn Leu Lys Leu Val Val Ala Gly Val Gly Ser Asp
                 85                  90                  95
His Ile Asp Leu Asp Tyr Ile Asn Gln Thr Gly Lys Lys Ile Ser Val
                100                 105                 110
Leu Glu Val Thr Gly Ser Asn Val Val Ser Val Ala Glu His Val Val
            115                 120                 125
Met Thr Met Leu Val Leu Val Arg Asn Phe Val Pro Ala His Glu Gln
        130                 135                 140
Ile Ile Asn His Asp Trp Glu Val Ala Ala Ile Ala Lys Asp Ala Tyr
145                 150                 155                 160
Asp Ile Glu Gly Lys Thr Ile Ala Thr Ile Gly Ala Gly Arg Ile Gly
                165                 170                 175
Tyr Arg Val Leu Glu Arg Leu Leu Pro Phe Asn Pro Lys Glu Leu Leu
            180                 185                 190
Tyr Tyr Asp Tyr Gln Ala Leu Pro Lys Glu Ala Glu Glu Lys Val Gly
        195                 200                 205
Ala Arg Arg Val Glu Asn Ile Glu Glu Leu Val Ala Gln Ala Asp Ile
    210                 215                 220
Val Thr Val Asn Ala Pro Leu His Ala Gly Thr Lys Gly Leu Ile Asn
225                 230                 235                 240
Lys Glu Leu Leu Ser Lys Phe Lys Lys Gly Ala Trp Leu Val Asn Thr
                245                 250                 255
Ala Arg Gly Ala Ile Ser Val Ala Glu Asp Val Ala Ala Ala Leu Glu
            260                 265                 270
Ser Gly Gln Leu Arg Gly Tyr Gly Gly Asp Val Trp Phe Pro Gln Pro
        275                 280                 285
Ala Pro Lys Asp His Pro Trp Arg Asp Met Arg Asn Lys Tyr Gly Ala
    290                 295                 300
Gly Asn Ala Met Thr Pro His Tyr Ser Gly Thr Thr Leu Asp Ala Gln
305                 310                 315                 320
Thr Arg Tyr Ala Glu Gly Thr Lys Asn Ile Leu Glu Ser Phe Phe Thr
                325                 330                 335
Gly Lys Phe Asp Tyr Arg Pro Gln Asp Ile Ile Leu Leu Asn Gly Glu
            340                 345                 350
Tyr Val Thr Lys Ala Tyr Gly Lys His Asp Lys Lys
        355                 360

<210> SEQ ID NO: 9
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 9 atg aag att gtc tta gtt ctt tat gat gct ggt aag cac gct gct gat          48
```

```
Met Lys Ile Val Leu Val Leu Tyr Asp Ala Gly Lys His Ala Ala Asp
 1               5                  10                  15 gaa gaa aaa tta tat ggt tgt act gaa aat aaa tta ggt att gcc aat         96
Glu Glu Lys Leu Tyr Gly Cys Thr Glu Asn Lys Leu Gly Ile Ala Asn
             20                  25                  30 tgg tta aaa gat caa ggt cat gaa cta att act act tct gat aaa gaa        144
Trp Leu Lys Asp Gln Gly His Glu Leu Ile Thr Thr Ser Asp Lys Glu
         35                  40                  45 ggt gaa aca agc gaa ttg gat aaa cat atc cca gat gct gat att atc        192
Gly Glu Thr Ser Glu Leu Asp Lys His Ile Pro Asp Ala Asp Ile Ile
     50                  55                  60 atc acc act cct ttc cat cct gct tat atc act aag gaa aga ctt gac        240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat        288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc        336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc        384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa        432
Met Thr Met Leu Val Leu Val Arg Asn Phe Val Pro Ala His Glu Gln
130                 135                 140 att att aac cac gat tgg gag gtt gct gct atc gct aag gat gct tac        480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt        528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta        576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt        624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc        672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat        720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc        768
Lys Glu Leu Leu Ser Lys Phe Lys Lys Gly Ala Trp Leu Val Asn Thr
                245                 250                 255 gca aga ggt gct att gtc gtt gct gaa gat gtt gca gca gct tta gaa        816
Ala Arg Gly Ala Ile Val Val Ala Glu Asp Val Ala Ala Ala Leu Glu
            260                 265                 270 tct ggt caa tta aga ggt tac ggt ggt gat gtt tgg ttc cca caa cca        864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct        912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa        960
Gly Asn Ala Met Thr Pro His Tyr Ser Gly Thr Thr Leu Asp Ala Gln
305                 310                 315                 320
```

| | | |
|---|---|---|
| aca aga tac gct gaa ggt act aaa aat att ttg gaa tca ttc ttt acc<br>Thr Arg Tyr Ala Glu Gly Thr Lys Asn Ile Leu Glu Ser Phe Phe Thr<br>325                        330                  335 | 1008 |
| ggt aaa ttt gat tac aga cca caa gat att atc tta tta aat ggg gaa<br>Gly Lys Phe Asp Tyr Arg Pro Gln Asp Ile Ile Leu Leu Asn Gly Glu<br>340                        345                  350 | 1056 |
| tac gtt act aaa gct tac ggt aaa cac gat aag aaa tag<br>Tyr Val Thr Lys Ala Tyr Gly Lys His Asp Lys Lys<br>355                        360 | 1095 |

<210> SEQ ID NO: 10
<211> LENGTH: 364
<212> TYPE: PRT
<213> ORGANISM: Candida boidinii

<400> SEQUENCE: 10

Met Lys Ile Val Leu Val Leu Tyr Asp Ala Gly Lys His Ala Ala Asp
  1                 5                   10                15

Glu Lys Leu Tyr Gly Cys Thr Glu Asn Lys Leu Gly Ile Ala Asn
              20                 25                 30

Trp Leu Lys Asp Gln Gly His Glu Leu Ile Thr Thr Ser Asp Lys Glu
           35                 40                 45

Gly Glu Thr Ser Glu Leu Asp Lys His Ile Pro Asp Ala Asp Ile Ile
 50                    55                   60

Ile Thr Thr Pro Phe His Pro Ala Tyr Ile Thr Lys Glu Arg Leu Asp
65                  70                   75                80

Lys Ala Lys Asn Leu Lys Leu Val Val Ala Gly Val Gly Ser Asp
              85                 90                 95

His Ile Asp Leu Asp Tyr Ile Asn Gln Thr Gly Lys Lys Ile Ser Val
           100                105               110

Leu Glu Val Thr Gly Ser Asn Val Val Ser Val Ala Glu His Val Val
        115                120               125

Met Thr Met Leu Val Leu Val Arg Asn Phe Val Pro Ala His Glu Gln
     130                135               140

Ile Ile Asn His Asp Trp Glu Val Ala Ala Ile Ala Lys Asp Ala Tyr
145                150                 155              160

Asp Ile Glu Gly Lys Thr Ile Ala Thr Ile Gly Ala Gly Arg Ile Gly
           165                170               175

Tyr Arg Val Leu Glu Arg Leu Leu Pro Phe Asn Pro Lys Glu Leu Leu
        180                185               190

Tyr Tyr Asp Tyr Gln Ala Leu Pro Lys Glu Ala Glu Lys Val Gly
     195                200               205

Ala Arg Arg Val Glu Asn Ile Glu Glu Leu Val Ala Gln Ala Asp Ile
     210                215               220

Val Thr Val Asn Ala Pro Leu His Ala Gly Thr Lys Gly Leu Ile Asn
225                230                 235              240

Lys Glu Leu Leu Ser Lys Phe Lys Lys Gly Ala Trp Leu Val Asn Thr
           245                250               255

Ala Arg Gly Ala Ile Val Val Ala Glu Asp Val Ala Ala Leu Glu
             260               265               270

Ser Gly Gln Leu Arg Gly Tyr Gly Gly Asp Val Trp Phe Pro Gln Pro
        275                280               285

Ala Pro Lys Asp His Pro Trp Arg Asp Met Arg Asn Lys Tyr Gly Ala
     290                295               300

Gly Asn Ala Met Thr Pro His Tyr Ser Gly Thr Thr Leu Asp Ala Gln
305                310                 315              320

```
Thr Arg Tyr Ala Glu Gly Thr Lys Asn Ile Leu Glu Ser Phe Phe Thr
            325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360

<210> SEQ ID NO: 11
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 11 atg aag att gtc tta gtt ctt tat gat gct ggt aag cac gct gct gat      48
Met Lys Ile Val Leu Val Leu Tyr Asp Ala Gly Lys His Ala Ala Asp
  1               5                  10                  15 gaa gaa aaa tta tat ggt tgt act gaa aat aaa tta ggt att gcc aat      96
Glu Glu Lys Leu Tyr Gly Cys Thr Glu Asn Lys Leu Gly Ile Ala Asn
             20                  25                  30 tgg tta aaa gat caa ggt cat gaa cta att act act tct gat aaa gaa     144
Trp Leu Lys Asp Gln Gly His Glu Leu Ile Thr Thr Ser Asp Lys Glu
         35                  40                  45 ggt gaa aca agc gaa ttg gat aaa cat atc cca gat gct gat att atc     192
Gly Glu Thr Ser Glu Leu Asp Lys His Ile Pro Asp Ala Asp Ile Ile
     50                  55                  60 atc acc act cct ttc cat cct gct tat atc act aag gaa aga ctt gac     240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat     288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc     336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc     384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa     432
Met Thr Met Leu Val Leu Val Arg Asn Phe Val Pro Ala His Glu Gln
    130                 135                 140 att att aac cac gat tgg gag gtt gct gct atc gct aag gat gct tac     480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt     528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta     576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt     624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc     672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat     720
Val Thr Val Asn Ala Pro Leu His Ala Gly Thr Lys Gly Leu Ile Asn
```

-continued

```
                225                 230                 235                 240
aag gaa tta tta tct aaa ttt aaa aaa ggt gct tgg tta gtc aat acc    768
Lys Glu Leu Leu Ser Lys Phe Lys Lys Gly Ala Trp Leu Val Asn Thr
                245                 250                 255 gca aga ggt gct att gct gtt gct gaa gat gtt gca gca gct tta gaa    816
Ala Arg Gly Ala Ile Ala Val Ala Glu Asp Val Ala Ala Ala Leu Glu
            260                 265                 270 tct ggt caa tta aga ggt tac ggt ggt gat gtt tgg ttc cca caa cca    864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct    912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa    960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc   1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa   1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag               1095
Tyr Val Thr Lys Ala Tyr Gly Lys His Asp Lys Lys
        355                 360

<210> SEQ ID NO: 12
<211> LENGTH: 364
<212> TYPE: PRT
<213> ORGANISM: Candida boidinii

<400> SEQUENCE: 12

Met Lys Ile Val Leu Val Leu Tyr Asp Ala Gly Lys His Ala Ala Asp
  1               5                  10                  15

Glu Glu Lys Leu Tyr Gly Cys Thr Glu Asn Lys Leu Gly Ile Ala Asn
                 20                  25                  30

Trp Leu Lys Asp Gln Gly His Glu Leu Ile Thr Thr Ser Asp Lys Glu
             35                  40                  45

Gly Glu Thr Ser Glu Leu Asp Lys His Ile Pro Asp Ala Asp Ile Ile
         50                  55                  60

Ile Thr Thr Pro Phe His Pro Ala Tyr Ile Thr Lys Glu Arg Leu Asp
 65                  70                  75                  80

Lys Ala Lys Asn Leu Lys Leu Val Val Val Ala Gly Val Gly Ser Asp
                 85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Glu Lys Val Gly
```

```
                195                 200                 205
Ala Arg Arg Val Glu Asn Ile Glu Glu Leu Val Ala Gln Ala Asp Ile
    210                 215                 220
Val Thr Val Asn Ala Pro Leu His Ala Gly Thr Lys Gly Leu Ile Asn
225                 230                 235                 240
Lys Glu Leu Leu Ser Lys Phe Lys Lys Gly Ala Trp Leu Val Asn Thr
                245                 250                 255
Ala Arg Gly Ala Ile Ala Val Ala Glu Asp Val Ala Ala Leu Glu
    260                 265                 270
Ser Gly Gln Leu Arg Gly Tyr Gly Asp Val Trp Phe Pro Gln Pro
    275                 280                 285
Ala Pro Lys Asp His Pro Trp Arg Asp Met Arg Asn Lys Tyr Gly Ala
    290                 295                 300
Gly Asn Ala Met Thr Pro His Tyr Ser Gly Thr Thr Leu Asp Ala Gln
305                 310                 315                 320
Thr Arg Tyr Ala Glu Gly Thr Lys Asn Ile Leu Glu Ser Phe Phe Thr
                325                 330                 335
Gly Lys Phe Asp Tyr Arg Pro Gln Asp Ile Ile Leu Leu Asn Gly Glu
                340                 345                 350
Tyr Val Thr Lys Ala Tyr Gly Lys His Asp Lys Lys
                355                 360
```

<210> SEQ ID NO: 13
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 13

```
atg aag att gtc tta gtt ctt tat gat gct ggt aag cac gct gct gat      48
Met Lys Ile Val Leu Val Leu Tyr Asp Ala Gly Lys His Ala Ala Asp
 1               5                  10                  15 gaa gaa aaa tta tat ggt tct act gaa aat aaa tta ggt att gcc aat      96
Glu Glu Lys Leu Tyr Gly Ser Thr Glu Asn Lys Leu Gly Ile Ala Asn
                20                  25                  30 tgg tta aaa gat caa ggt cat gaa cta att act act tct gat aaa gaa     144
Trp Leu Lys Asp Gln Gly His Glu Leu Ile Thr Thr Ser Asp Lys Glu
            35                  40                  45 ggt gaa aca agc gaa ttg gat aaa cat atc cca gat gct gat att atc     192
Gly Glu Thr Ser Glu Leu Asp Lys His Ile Pro Asp Ala Asp Ile Ile
        50                  55                  60 atc acc act cct ttc cat cct gct tat atc act aag gaa aga ctt gac     240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat     288
Lys Ala Lys Asn Leu Lys Leu Val Val Val Ala Gly Val Gly Ser Asp
                85                  90                  95 cac att gat tta gat tat att aat caa aca ggt aag aaa atc tca gtc     336
His Ile Asp Leu Asp Tyr Ile Asn Gln Thr Gly Lys Lys Ile Ser Val
                100                 105                 110 ctg gaa gtt aca ggt tct aat gtt gtc tct gtt gct gaa cac gtt gtc     384
Leu Glu Val Thr Gly Ser Asn Val Val Ser Val Ala Glu His Val Val
            115                 120                 125 atg acc atg ctt gtc ttg gtt aga aat ttc gtt cca gca cat gaa caa     432
Met Thr Met Leu Val Leu Val Arg Asn Phe Val Pro Ala His Glu Gln
        130                 135                 140
```

-continued

| | |
|---|---|
| att att aac cac gat tgg gag gtt gct gct atc gct aag gat gct tac<br>Ile Ile Asn His Asp Trp Glu Val Ala Ala Ile Ala Lys Asp Ala Tyr<br>145                  150                  155                  160 | 480 |
| gat atc gaa ggt aaa act atc gct acc att ggt gct ggt aga att ggt<br>Asp Ile Glu Gly Lys Thr Ile Ala Thr Ile Gly Ala Gly Arg Ile Gly<br>165                  170                  175 | 528 |
| tac aga gtc ttg gaa aga tta ctc cca ttt aat cca aaa gaa tta tta<br>Tyr Arg Val Leu Glu Arg Leu Leu Pro Phe Asn Pro Lys Glu Leu Leu<br>180                  185                  190 | 576 |
| tac tac gat tat caa gct tta cca aaa gaa gct gaa gaa aaa gtt ggt<br>Tyr Tyr Asp Tyr Gln Ala Leu Pro Lys Glu Ala Glu Glu Lys Val Gly<br>        195                  200                  205 | 624 |
| gct aga aga gtt gaa aat att gaa gaa tta gtt gct caa gct gat atc<br>Ala Arg Arg Val Glu Asn Ile Glu Glu Leu Val Ala Gln Ala Asp Ile<br>210                  215                  220 | 672 |
| gtt aca gtt aat gct cca tta cac gca ggt aca aaa ggt tta att aat<br>Val Thr Val Asn Ala Pro Leu His Ala Gly Thr Lys Gly Leu Ile Asn<br>225                  230                  235                  240 | 720 |
| aag gaa tta tta tct aaa ttt aaa aaa ggt gct tgg tta gtc aat acc<br>Lys Glu Leu Leu Ser Lys Phe Lys Lys Gly Ala Trp Leu Val Asn Thr<br>        245                  250                  255 | 768 |
| gca aga ggt gct att tct gtt gct gaa gat gtt gca gca gct tta gaa<br>Ala Arg Gly Ala Ile Ser Val Ala Glu Asp Val Ala Ala Ala Leu Glu<br>260                  265                  270 | 816 |
| tct ggt caa tta aga ggt tac ggt ggt gat gtt tgg ttc cca caa cca<br>Ser Gly Gln Leu Arg Gly Tyr Gly Gly Asp Val Trp Phe Pro Gln Pro<br>275                  280                  285 | 864 |
| gct cca aag gat cac cca tgg aga gat atg aga aat aaa tat ggt gct<br>Ala Pro Lys Asp His Pro Trp Arg Asp Met Arg Asn Lys Tyr Gly Ala<br>290                  295                  300 | 912 |
| ggt aat gcc atg act cct cac tac tct ggt act act tta gac gct caa<br>Gly Asn Ala Met Thr Pro His Tyr Ser Gly Thr Thr Leu Asp Ala Gln<br>305                  310                  315                  320 | 960 |
| aca aga tac gct gaa ggt act aaa aat att ttg gaa tca ttc ttt acc<br>Thr Arg Tyr Ala Glu Gly Thr Lys Asn Ile Leu Glu Ser Phe Phe Thr<br>        325                  330                  335 | 1008 |
| ggt aaa ttt gat tac aga cca caa gat att atc tta tta aat ggg gaa<br>Gly Lys Phe Asp Tyr Arg Pro Gln Asp Ile Ile Leu Leu Asn Gly Glu<br>340                  345                  350 | 1056 |
| tac gtt act aaa gct tac ggt aaa cac gat aag aaa tag<br>Tyr Val Thr Lys Ala Tyr Gly Lys His Asp Lys Lys<br>        355                  360 | 1095 |

<210> SEQ ID NO: 14
<211> LENGTH: 364
<212> TYPE: PRT
<213> ORGANISM: Candida boidinii

<400> SEQUENCE: 14

Met Lys Ile Val Leu Val Leu Tyr Asp Ala Gly Lys His Ala Ala Asp
1                  5                      10                      15

Glu Glu Lys Leu Tyr Gly Ser Thr Glu Asn Lys Leu Gly Ile Ala Asn
                  20                      25                      30

Trp Leu Lys Asp Gln Gly His Glu Leu Ile Thr Thr Ser Asp Lys Glu
              35                      40                      45

Gly Glu Thr Ser Glu Leu Asp Lys His Ile Pro Asp Ala Asp Ile Ile
        50                  55                      60

Ile Thr Thr Pro Phe His Pro Ala Tyr Ile Thr Lys Glu Arg Leu Asp
65                  70                  75                  80

```
Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
            195                 200                 205

Ala Arg Arg Val Glu Asn Ile Glu Glu Leu Val Ala Gln Ala Asp Ile
210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Ser Val Ala Glu Asp Val Ala Ala Ala Leu Glu
            260                 265                 270

Ser Gly Gln Leu Arg Gly Tyr Gly Gly Asp Val Trp Phe Pro Gln Pro
            275                 280                 285

Ala Pro Lys Asp His Pro Trp Arg Asp Met Arg Asn Lys Tyr Gly Ala
290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360

<210> SEQ ID NO: 15
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 15 atg aag att gtc tta gtt ctt tat gat gct ggt aag cac gct gct gat        48
Met Lys Ile Val Leu Val Leu Tyr Asp Ala Gly Lys His Ala Ala Asp
  1               5                  10                  15 gaa gaa aaa tta tat ggt tct act gaa aat aaa tta ggt att gcc aat        96
Glu Glu Lys Leu Tyr Gly Ser Thr Glu Asn Lys Leu Gly Ile Ala Asn
                 20                  25                  30 tgg tta aaa gat caa ggt cat gaa cta att act act tct gat aaa gaa       144
Trp Leu Lys Asp Gln Gly His Glu Leu Ile Thr Thr Ser Asp Lys Glu
             35                  40                  45 ggt gaa aca agc gaa ttg gat aaa cat atc cca gat gct gat att atc       192
Gly Glu Thr Ser Glu Leu Asp Lys His Ile Pro Asp Ala Asp Ile Ile
         50                  55                  60
```

```
             50                    55                    60
atc acc act cct ttc cat cct gct tat atc act aag gaa aga ctt gac      240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat      288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc      336
His Ile Asp Leu Asp Tyr Ile Asn Gln Thr Gly Lys Lys Ile Ser Val
                100                 105                 110 ctg gaa gtt aca ggt tct aat gtt gtc tct gtt gct gaa cac gtt gtc      384
Leu Glu Val Thr Gly Ser Asn Val Val Ser Val Ala Glu His Val Val
            115                 120                 125 atg acc atg ctt gtc ttg gtt aga aat ttc gtt cca gca cat gaa caa      432
Met Thr Met Leu Val Leu Val Arg Asn Phe Val Pro Ala His Glu Gln
        130                 135                 140 att att aac cac gat tgg gag gtt gct gct atc gct aag gat gct tac      480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt      528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta      576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt      624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc      672
Ala Arg Arg Val Glu Asn Ile Glu Glu Leu Val Ala Gln Ala Asp Ile
210                 215                 220 gtt aca gtt aat gct cca tta cac gca ggt aca aaa ggt tta att aat      720
Val Thr Val Asn Ala Pro Leu His Ala Gly Thr Lys Gly Leu Ile Asn
                225                 230                 235                 240 aag gaa tta tta tct aaa ttt aaa aaa ggt gct tgg tta gtc aat acc      768
Lys Glu Leu Leu Ser Lys Phe Lys Lys Gly Ala Trp Leu Val Asn Thr
            245                 250                 255 gca aga ggt gct att gct gtt gct gaa gat gtt gca gca gct tta gaa      816
Ala Arg Gly Ala Ile Ala Val Ala Glu Asp Val Ala Ala Ala Leu Glu
        260                 265                 270 tct ggt caa tta aga ggt tac ggt ggt gat gtt tgg ttc cca caa cca      864
Ser Gly Gln Leu Arg Gly Tyr Gly Gly Asp Val Trp Phe Pro Gln Pro
275                 280                 285 gct cca aag gat cac cca tgg aga gat atg aga aat aaa tat ggt gct      912
Ala Pro Lys Asp His Pro Trp Arg Asp Met Arg Asn Lys Tyr Gly Ala
                290                 295                 300 ggt aat gcc atg act cct cac tac tct ggt act act tta gac gct caa      960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc     1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa     1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag                 1095
Tyr Val Thr Lys Ala Tyr Gly Lys His Asp Lys Lys
        355                 360
```

-continued

```
<210> SEQ ID NO: 16
<211> LENGTH: 364
<212> TYPE: PRT
<213> ORGANISM: Candida boidinii

<400> SEQUENCE: 16

Met Lys Ile Val Leu Val Leu Tyr Asp Ala Gly Lys His Ala Ala Asp
 1               5                  10                  15

Glu Glu Lys Leu Tyr Gly Ser Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
        50                  55                  60

Ile Thr Thr Pro Phe His Pro Ala Tyr Ile Thr Lys Glu Arg Leu Asp
 65                 70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Ala Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO: 17
<211> LENGTH: 1095
```

```
<212> TYPE: DNA
<213> ORGANISM: Candida boidinii
<220> FEATURE:
<221> NAME/KEY: CDS
<222> LOCATION: (1)..(1092)

<400> SEQUENCE: 17 atg aag att gtc tta gtt ctt tat gat gct ggt aag cac gct gct gat         48
Met Lys Ile Val Leu Val Leu Tyr Asp Ala Gly Lys His Ala Ala Asp
 1               5                  10                  15 gaa gaa aaa tta tat ggt tct act gaa aat aaa tta ggt att gcc aat         96
Glu Glu Lys Leu Tyr Gly Ser Thr Glu Asn Lys Leu Gly Ile Ala Asn
             20                  25                  30 tgg tta aaa gat caa ggt cat gaa cta att act act tct gat aaa gaa        144
Trp Leu Lys Asp Gln Gly His Glu Leu Ile Thr Thr Ser Asp Lys Glu
         35                  40                  45 ggt gaa aca agc gaa ttg gat aaa cat atc cca gat gct gat att atc        192
Gly Glu Thr Ser Glu Leu Asp Lys His Ile Pro Asp Ala Asp Ile Ile
     50                  55                  60 atc acc act cct ttc cat cct gct tat atc act aag gaa aga ctt gac        240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat        288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc        336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc        384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa        432
Met Thr Met Leu Val Leu Val Arg Asn Phe Val Pro Ala His Glu Gln
130                 135                 140 att att aac cac gat tgg gag gtt gct gct atc gct aag gat gct tac        480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt        528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta        576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt        624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc        672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat        720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc        768
Lys Glu Leu Leu Ser Lys Phe Lys Lys Gly Ala Trp Leu Val Asn Thr
                245                 250                 255 gca aga ggt gct att gtc gtt gct gaa gat gtt gca gca gct tta gaa        816
Ala Arg Gly Ala Ile Val Val Ala Glu Asp Val Ala Ala Ala Leu Glu
            260                 265                 270 tct ggt caa tta aga ggt tac ggt ggt gat gtt tgg ttc cca caa cca        864
Ser Gly Gln Leu Arg Gly Tyr Gly Gly Asp Val Trp Phe Pro Gln Pro
        275                 280                 285
```

```
gct cca aag gat cac cca tgg aga gat atg aga aat aaa tat ggt gct      912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa      960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc     1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa     1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag                 1095
Tyr Val Thr Lys Ala Tyr Gly Lys His Asp Lys Lys
                355                 360
```

<210> SEQ ID NO: 18
<211> LENGTH: 364
<212> TYPE: PRT
<213> ORGANISM: Candida boidinii

<400> SEQUENCE: 18

```
Met Lys Ile Val Leu Val Leu Tyr Asp Ala Gly Lys His Ala Ala Asp
 1               5                  10                  15

Glu Glu Lys Leu Tyr Gly Ser Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Val Val Ala Glu Asp Val Ala Ala Ala Leu Glu
            260                 265                 270
```

```
Ser Gly Gln Leu Arg Gly Tyr Gly Gly Asp Val Trp Phe Pro Gln Pro
            275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360
```

<210> SEQ ID NO: 19
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 19

```
atg aag att gtc tta gtt ctt tat gat gct ggt aag cac gct gct gat        48
Met Lys Ile Val Leu Val Leu Tyr Asp Ala Gly Lys His Ala Ala Asp
  1               5                  10                  15 gaa gaa aaa tta tat ggt gct act gaa aat aaa tta ggt att gcc aat        96
Glu Glu Lys Leu Tyr Gly Ala Thr Glu Asn Lys Leu Gly Ile Ala Asn
             20                  25                  30 tgg tta aaa gat caa ggt cat gaa cta att act act tct gat aaa gaa       144
Trp Leu Lys Asp Gln Gly His Glu Leu Ile Thr Thr Ser Asp Lys Glu
         35                  40                  45 ggt gaa aca agc gaa ttg gat aaa cat atc cca gat gct gat att atc       192
Gly Glu Thr Ser Glu Leu Asp Lys His Ile Pro Asp Ala Asp Ile Ile
     50                  55                  60 atc acc act cct ttc cat cct gct tat atc act aag gaa aga ctt gac       240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat       288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc       336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc       384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa       432
Met Thr Met Leu Val Leu Val Arg Asn Phe Val Pro Ala His Glu Gln
    130                 135                 140 att att aac cac gat tgg gag gtt gct gct atc gct aag gat gct tac       480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt       528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta       576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt       624
Tyr Tyr Asp Tyr Gln Ala Leu Pro Lys Glu Ala Glu Glu Lys Val Gly
```

-continued

```
Tyr Tyr Asp Tyr Gln Ala Leu Pro Lys Glu Ala Glu Lys Val Gly
            195                 200                 205 gct aga aga gtt gaa aat att gaa gaa tta gtt gct caa gct gat atc     672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat     720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc     768
Lys Glu Leu Leu Ser Lys Phe Lys Lys Gly Ala Trp Leu Val Asn Thr
                245                 250                 255 gca aga ggt gct att tct gtt gct gaa gat gtt gca gca gct tta gaa     816
Ala Arg Gly Ala Ile Ser Val Ala Glu Asp Val Ala Ala Ala Leu Glu
            260                 265                 270 tct ggt caa tta aga ggt tac ggt ggt gat gtt tgg ttc cca caa cca     864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct     912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa     960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc    1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa    1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag               1095
Tyr Val Thr Lys Ala Tyr Gly Lys His Asp Lys Lys
        355                 360
```

<210> SEQ ID NO: 20
<211> LENGTH: 364
<212> TYPE: PRT
<213> ORGANISM: Candida boidinii

<400> SEQUENCE: 20

```
Met Lys Ile Val Leu Val Leu Tyr Asp Ala Gly Lys His Ala Ala Asp
1               5                   10                  15

Glu Glu Lys Leu Tyr Gly Ala Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
```

```
145                 150                 155                 160
Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Ser Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO: 21
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 21 atg aag att gtc tta gtt ctt tat gat gct ggt aag cac gct gct gat    48
Met Lys Ile Val Leu Val Leu Tyr Asp Ala Gly Lys His Ala Ala Asp
 1               5                  10                  15 gaa gaa aaa tta tat ggt gct act gaa aat aaa tta ggt att gcc aat    96
Glu Glu Lys Leu Tyr Gly Ala Thr Glu Asn Lys Leu Gly Ile Ala Asn
            20                  25                  30 tgg tta aaa gat caa ggt cat gaa cta att act act tct gat aaa gaa   144
Trp Leu Lys Asp Gln Gly His Glu Leu Ile Thr Thr Ser Asp Lys Glu
        35                  40                  45 ggt gaa aca agc gaa ttg gat aaa cat atc cca gat gct gat att atc   192
Gly Glu Thr Ser Glu Leu Asp Lys His Ile Pro Asp Ala Asp Ile Ile
    50                  55                  60 atc acc act cct ttc cat cct gct tat atc act aag gaa aga ctt gac   240
Ile Thr Thr Pro Phe His Pro Ala Tyr Ile Thr Lys Glu Arg Leu Asp
65                  70                  75                  80 aag gct aag aac tta aaa tta gtc gtt gtc gct ggt gtt ggt tct gat   288
Lys Ala Lys Asn Leu Lys Leu Val Val Val Ala Gly Val Gly Ser Asp
                85                  90                  95 cac att gat tta gat tat att aat caa aca ggt aag aaa atc tca gtc   336
His Ile Asp Leu Asp Tyr Ile Asn Gln Thr Gly Lys Lys Ile Ser Val
            100                 105                 110
```

```
ctg gaa gtt aca ggt tct aat gtt gtc tct gtt gct gaa cac gtt gtc    384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa    432
Met Thr Met Leu Val Leu Val Arg Asn Phe Val Pro Ala His Glu Gln
    130                 135                 140 att att aac cac gat tgg gag gtt gct gct atc gct aag gat gct tac    480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt    528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta    576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt    624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc    672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat    720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc    768
Lys Glu Leu Leu Ser Lys Phe Lys Lys Gly Ala Trp Leu Val Asn Thr
                245                 250                 255 gca aga ggt gct att gct gtt gct gaa gat gtt gca gca gct tta gaa    816
Ala Arg Gly Ala Ile Ala Val Ala Glu Asp Val Ala Ala Ala Leu Glu
            260                 265                 270 tct ggt caa tta aga ggt tac ggt ggt gat gtt tgg ttc cca caa cca    864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct    912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa    960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc   1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa   1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag               1095
Tyr Val Thr Lys Ala Tyr Gly Lys His Asp Lys Lys
        355                 360

<210> SEQ ID NO: 22
<211> LENGTH: 364
<212> TYPE: PRT
<213> ORGANISM: Candida boidinii

<400> SEQUENCE: 22

Met Lys Ile Val Leu Val Leu Tyr Asp Ala Gly Lys His Ala Ala Asp
 1               5                   10                  15

Glu Glu Lys Leu Tyr Gly Ala Thr Glu Asn Lys Leu Gly Ile Ala Asn
            20                  25                  30
```

```
Trp Leu Lys Asp Gln Gly His Glu Leu Ile Thr Thr Ser Asp Lys Glu
         35                  40                  45

Gly Glu Thr Ser Glu Leu Asp Lys His Ile Pro Asp Ala Asp Ile Ile
 50                  55                  60

Ile Thr Thr Pro Phe His Pro Ala Tyr Ile Thr Lys Glu Arg Leu Asp
 65                  70                  75                  80

Lys Ala Lys Asn Leu Lys Leu Val Val Ala Gly Val Gly Ser Asp
                 85                  90                  95

His Ile Asp Leu Asp Tyr Ile Asn Gln Thr Gly Lys Lys Ile Ser Val
                100                 105                 110

Leu Glu Val Thr Gly Ser Asn Val Val Ser Val Ala Glu His Val Val
             115                 120                 125

Met Thr Met Leu Val Leu Val Arg Asn Phe Val Pro Ala His Glu Gln
 130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
            195                 200                 205

Ala Arg Arg Val Glu Asn Ile Glu Glu Leu Val Ala Gln Ala Asp Ile
210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Ala Val Ala Glu Asp Val Ala Ala Ala Leu Glu
            260                 265                 270

Ser Gly Gln Leu Arg Gly Tyr Gly Gly Asp Val Trp Phe Pro Gln Pro
275                 280                 285

Ala Pro Lys Asp His Pro Trp Arg Asp Met Arg Asn Lys Tyr Gly Ala
290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360

<210> SEQ ID NO: 23
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 23 atg aag att gtc tta gtt ctt tat gat gct ggt aag cac gct gct gat        48
Met Lys Ile Val Leu Val Leu Tyr Asp Ala Gly Lys His Ala Ala Asp
 1               5                  10                  15 gaa gaa aaa tta tat ggt gct act gaa aat aaa tta ggt att gcc aat        96
```

-continued

```
                Glu Glu Lys Leu Tyr Gly Ala Thr Glu Asn Lys Leu Gly Ile Ala Asn
                         20                  25                  30 tgg tta aaa gat caa ggt cat gaa cta att act act tct gat aaa gaa       144
Trp Leu Lys Asp Gln Gly His Glu Leu Ile Thr Thr Ser Asp Lys Glu
         35                  40                  45 ggt gaa aca agc gaa ttg gat aaa cat atc cca gat gct gat att atc       192
Gly Glu Thr Ser Glu Leu Asp Lys His Ile Pro Asp Ala Asp Ile Ile
 50                  55                  60 atc acc act cct ttc cat cct gct tat atc act aag gaa aga ctt gac       240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat       288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc       336
His Ile Asp Leu Asp Tyr Ile Asn Gln Thr Gly Lys Lys Ile Ser Val
                100                 105                 110 ctg gaa gtt aca ggt tct aat gtt gtc tct gtt gct gaa cac gtt gtc       384
Leu Glu Val Thr Gly Ser Asn Val Val Ser Val Ala Glu His Val Val
            115                 120                 125 atg acc atg ctt gtc ttg gtt aga aat ttc gtt cca gca cat gaa caa       432
Met Thr Met Leu Val Leu Val Arg Asn Phe Val Pro Ala His Glu Gln
        130                 135                 140 att att aac cac gat tgg gag gtt gct gct atc gct aag gat gct tac       480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt       528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta       576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt       624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc       672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat       720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc       768
Lys Glu Leu Leu Ser Lys Phe Lys Lys Gly Ala Trp Leu Val Asn Thr
                245                 250                 255 gca aga ggt gct att gtc gtt gct gaa gat gtt gca gca gct tta gaa       816
Ala Arg Gly Ala Ile Val Val Ala Glu Asp Val Ala Ala Ala Leu Glu
            260                 265                 270 tct ggt caa tta aga ggt tac ggt ggt gat gtt tgg ttc cca caa cca       864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct       912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa       960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc      1008
Thr Arg Tyr Ala Glu Gly Thr Lys Asn Ile Leu Glu Ser Phe Phe Thr
                325                 330                 335
```

-continued

```
ggt aaa ttt gat tac aga cca caa gat att atc tta tta aat ggg gaa    1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag                1095
Tyr Val Thr Lys Ala Tyr Gly Lys His Asp Lys Lys
    355                 360
```

<210> SEQ ID NO: 24
<211> LENGTH: 364
<212> TYPE: PRT
<213> ORGANISM: Candida boidinii

<400> SEQUENCE: 24

```
Met Lys Ile Val Leu Val Leu Tyr Asp Ala Gly Lys His Ala Ala Asp
  1               5                  10                  15

Glu Lys Leu Tyr Gly Ala Thr Glu Asn Lys Leu Gly Ile Ala Asn
             20                  25                  30

Trp Leu Lys Asp Gln Gly His Glu Leu Ile Thr Thr Ser Asp Lys Glu
         35                  40                  45

Gly Glu Thr Ser Glu Leu Asp Lys His Ile Pro Asp Ala Asp Ile Ile
     50                  55                  60

Ile Thr Thr Pro Phe His Pro Ala Tyr Ile Thr Lys Glu Arg Leu Asp
 65                  70                  75                  80

Lys Ala Lys Asn Leu Lys Leu Val Val Val Ala Gly Val Gly Ser Asp
                 85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Val Ala Glu Asp Val Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335
```

-continued

```
Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360

<210> SEQ ID NO: 25
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 25 atg aag att gtc tta gtt ctt tat gat gct ggt aag cac gct gct gat      48
Met Lys Ile Val Leu Val Leu Tyr Asp Ala Gly Lys His Ala Ala Asp
  1               5                  10                  15 gaa gaa aaa tta tat ggt gtt act gaa aat aaa tta ggt att gcc aat      96
Glu Glu Lys Leu Tyr Gly Val Thr Glu Asn Lys Leu Gly Ile Ala Asn
                 20                  25                  30 tgg tta aaa gat caa ggt cat gaa cta att act act tct gat aaa gaa     144
Trp Leu Lys Asp Gln Gly His Glu Leu Ile Thr Thr Ser Asp Lys Glu
             35                  40                  45 ggt gaa aca agc gaa ttg gat aaa cat atc cca gat gct gat att atc     192
Gly Glu Thr Ser Glu Leu Asp Lys His Ile Pro Asp Ala Asp Ile Ile
         50                  55                  60 atc acc act cct ttc cat cct gct tat atc act aag gaa aga ctt gac     240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat     288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc     336
His Ile Asp Leu Asp Tyr Ile Asn Gln Thr Gly Lys Lys Ile Ser Val
                100                 105                 110 ctg gaa gtt aca ggt tct aat gtt gtc tct gtt gct gaa cac gtt gtc     384
Leu Glu Val Thr Gly Ser Asn Val Val Ser Val Ala Glu His Val Val
            115                 120                 125 atg acc atg ctt gtc ttg gtt aga aat ttc gtt cca gca cat gaa caa     432
Met Thr Met Leu Val Leu Val Arg Asn Phe Val Pro Ala His Glu Gln
        130                 135                 140 att att aac cac gat tgg gag gtt gct gct atc gct aag gat gct tac     480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt     528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta     576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt     624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc     672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat     720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc     768
Lys Glu Leu Leu Ser Lys Phe Lys Lys Gly Ala Trp Leu Val Asn Thr
```

```
                    245                 250                 255
gca aga ggt gct att gtc gtt gct gaa gat gtt gca gca gct tta gaa       816
Ala Arg Gly Ala Ile Val Val Ala Glu Asp Val Ala Ala Ala Leu Glu
        260                 265                 270 tct ggt caa tta aga ggt tac ggt ggt gat gtt tgg ttc cca caa cca       864
Ser Gly Gln Leu Arg Gly Tyr Gly Gly Asp Val Trp Phe Pro Gln Pro
            275                 280                 285 gct cca aag gat cac cca tgg aga gat atg aga aat aaa tat ggt gct       912
Ala Pro Lys Asp His Pro Trp Arg Asp Met Arg Asn Lys Tyr Gly Ala
        290                 295                 300 ggt aat gcc atg act cct cac tac tct ggt act act tta gac gct caa       960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc      1008
Thr Arg Tyr Ala Glu Gly Thr Lys Asn Ile Leu Glu Ser Phe Phe Thr
            325                 330                 335 ggt aaa ttt gat tac aga cca caa gat att atc tta tta aat ggg gaa      1056
Gly Lys Phe Asp Tyr Arg Pro Gln Asp Ile Ile Leu Leu Asn Gly Glu
        340                 345                 350 tac gtt act aaa gct tac ggt aaa cac gat aag aaa tag                  1095
Tyr Val Thr Lys Ala Tyr Gly Lys His Asp Lys Lys
            355                 360
```

<210> SEQ ID NO: 26
<211> LENGTH: 364
<212> TYPE: PRT
<213> ORGANISM: Candida boidinii

<400> SEQUENCE: 26

```
Met Lys Ile Val Leu Val Leu Tyr Asp Ala Gly Lys His Ala Ala Asp
  1               5                  10                  15

Glu Glu Lys Leu Tyr Gly Val Thr Glu Asn Lys Leu Gly Ile Ala Asn
                 20                  25                  30

Trp Leu Lys Asp Gln Gly His Glu Leu Ile Thr Thr Ser Asp Lys Glu
             35                  40                  45

Gly Glu Thr Ser Glu Leu Asp Lys His Ile Pro Asp Ala Asp Ile Ile
         50                  55                  60

Ile Thr Thr Pro Phe His Pro Ala Tyr Ile Thr Lys Glu Arg Leu Asp
 65                  70                  75                  80

Lys Ala Lys Asn Leu Lys Leu Val Val Val Ala Gly Val Gly Ser Asp
                 85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
210                 215                 220
```

```
Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
            245                 250                 255

Ala Arg Gly Ala Ile Val Val Ala Glu Asp Val Ala Ala Leu Glu
        260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
        290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
            325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360
```

<210> SEQ ID NO: 27
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 27

```
atg aag att gtc tta gtt ctt tat gat gct ggt aag cac gct gct gat        48
Met Lys Ile Val Leu Val Leu Tyr Asp Ala Gly Lys His Ala Ala Asp
1               5                   10                  15 gaa gaa aaa tta tat ggt gtt act gaa aat aaa tta ggt att gcc aat        96
Glu Glu Lys Leu Tyr Gly Val Thr Glu Asn Lys Leu Gly Ile Ala Asn
                20                  25                  30 tgg tta aaa gat caa ggt cat gaa cta att act act tct gat aaa gaa       144
Trp Leu Lys Asp Gln Gly His Glu Leu Ile Thr Thr Ser Asp Lys Glu
            35                  40                  45 ggt gaa aca agc gaa ttg gat aaa cat atc cca gat gct gat att atc       192
Gly Glu Thr Ser Glu Leu Asp Lys His Ile Pro Asp Ala Asp Ile Ile
    50                  55                  60 atc acc act cct ttc cat cct gct tat atc act aag gaa aga ctt gac       240
Ile Thr Thr Pro Phe His Pro Ala Tyr Ile Thr Lys Glu Arg Leu Asp
65                  70                  75                  80 aag gct aag aac tta aaa tta gtc gtt gtc gct ggt gtt ggt tct gat       288
Lys Ala Lys Asn Leu Lys Leu Val Val Val Ala Gly Val Gly Ser Asp
                85                  90                  95 cac att gat tta gat tat att aat caa aca ggt aag aaa atc tca gtc       336
His Ile Asp Leu Asp Tyr Ile Asn Gln Thr Gly Lys Lys Ile Ser Val
                100                 105                 110 ctg gaa gtt aca ggt tct aat gtt gtc tct gtt gct gaa cac gtt gtc       384
Leu Glu Val Thr Gly Ser Asn Val Val Ser Val Ala Glu His Val Val
            115                 120                 125 atg acc atg ctt gtc ttg gtt aga aat ttc gtt cca gca cat gaa caa       432
Met Thr Met Leu Val Leu Val Arg Asn Phe Val Pro Ala His Glu Gln
        130                 135                 140 att att aac cac gat tgg gag gtt gct gct atc gct aag gat gct tac       480
Ile Ile Asn His Asp Trp Glu Val Ala Ala Ile Ala Lys Asp Ala Tyr
145                 150                 155                 160
```

```
gat atc gaa ggt aaa act atc gct acc att ggt gct ggt aga att ggt       528
Asp Ile Glu Gly Lys Thr Ile Ala Thr Ile Gly Ala Gly Arg Ile Gly
            165                 170                 175 tac aga gtc ttg gaa aga tta ctc cca ttt aat cca aaa gaa tta tta       576
Tyr Arg Val Leu Glu Arg Leu Leu Pro Phe Asn Pro Lys Glu Leu Leu
        180                 185                 190 tac tac gat tat caa gct tta cca aaa gaa gct gaa gaa aaa gtt ggt       624
Tyr Tyr Asp Tyr Gln Ala Leu Pro Lys Glu Ala Glu Glu Lys Val Gly
    195                 200                 205 gct aga aga gtt gaa aat att gaa gaa tta gtt gct caa gct gat atc       672
Ala Arg Arg Val Glu Asn Ile Glu Glu Leu Val Ala Gln Ala Asp Ile
210                 215                 220 gtt aca gtt aat gct cca tta cac gca ggt aca aaa ggt tta att aat       720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc       768
Lys Glu Leu Leu Ser Lys Phe Lys Lys Gly Ala Trp Leu Val Asn Thr
                245                 250                 255 gca aga ggt gct att gct gtt gct gaa gat gtt gca gca gct tta gaa       816
Ala Arg Gly Ala Ile Ala Val Ala Glu Asp Val Ala Ala Ala Leu Glu
            260                 265                 270 tct ggt caa tta aga ggt tac ggt ggt gat gtt tgg ttc cca caa cca       864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct       912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa       960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc      1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa      1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag                  1095
Tyr Val Thr Lys Ala Tyr Gly Lys His Asp Lys Lys
        355                 360
```

<210> SEQ ID NO: 28
<211> LENGTH: 364
<212> TYPE: PRT
<213> ORGANISM: Candida boidinii

<400> SEQUENCE: 28

```
Met Lys Ile Val Leu Val Leu Tyr Asp Ala Gly Lys His Ala Ala Asp
 1               5                  10                  15

Glu Glu Lys Leu Tyr Gly Val Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
```

```
                    100                 105                 110
Leu Glu Val Thr Gly Ser Asn Val Ser Val Ala Glu His Val Val
            115                 120                 125

Met Thr Met Leu Val Leu Val Arg Asn Phe Val Pro Ala His Glu Gln
        130                 135                 140

Ile Ile Asn His Asp Trp Glu Val Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
            195                 200                 205

Ala Arg Arg Val Glu Asn Ile Glu Glu Leu Val Ala Gln Ala Asp Ile
        210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Ala Val Ala Glu Asp Val Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
        290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
            355                 360

<210> SEQ ID NO: 29
<211> LENGTH: 1095
<212> TYPE: DNA
<213> ORGANISM: Candida boidinii
<220> FEATURE:
<221> NAME/KEY: CDS
<222> LOCATION: (1)..(1092)

<400> SEQUENCE: 29 atg aag att gtc tta gtt ctt tat gat gct ggt aag cac gct gct gat    48
Met Lys Ile Val Leu Val Leu Tyr Asp Ala Gly Lys His Ala Ala Asp
1               5                   10                  15 gaa gaa aaa tta tat ggt gtt act gaa aat aaa tta ggt att gcc aat    96
Glu Glu Lys Leu Tyr Gly Val Thr Glu Asn Lys Leu Gly Ile Ala Asn
            20                  25                  30 tgg tta aaa gat caa ggt cat gaa cta att act act tct gat aaa gaa   144
Trp Leu Lys Asp Gln Gly His Glu Leu Ile Thr Thr Ser Asp Lys Glu
        35                  40                  45 ggt gaa aca agc gaa ttg gat aaa cat atc cca gat gct gat att atc   192
Gly Glu Thr Ser Glu Leu Asp Lys His Ile Pro Asp Ala Asp Ile Ile
    50                  55                  60 atc acc act cct ttc cat cct gct tat atc act aag gaa aga ctt gac   240
Ile Thr Thr Pro Phe His Pro Ala Tyr Ile Thr Lys Glu Arg Leu Asp
```

```
                65                  70                  75                  80
aag gct aag aac tta aaa tta gtc gtt gtc gct ggt gtt ggt tct gat     288
Lys Ala Lys Asn Leu Lys Leu Val Val Val Ala Gly Val Gly Ser Asp
                    85                  90                  95 cac att gat tta gat tat att aat caa aca ggt aag aaa atc tca gtc     336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc     384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa     432
Met Thr Met Leu Val Leu Val Arg Asn Phe Val Pro Ala His Glu Gln
    130                 135                 140 att att aac cac gat tgg gag gtt gct gct atc gct aag gat gct tac     480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt     528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta     576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt     624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc     672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat     720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc     768
Lys Glu Leu Leu Ser Lys Phe Lys Lys Gly Ala Trp Leu Val Asn Thr
                245                 250                 255 gca aga ggt gct att tct gtt gct gaa gat gtt gca gca gct tta gaa     816
Ala Arg Gly Ala Ile Ser Val Ala Glu Asp Val Ala Ala Ala Leu Glu
            260                 265                 270 tct ggt caa tta aga ggt tac ggt ggt gat gtt tgg ttc cca caa cca     864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct     912
Ala Pro Lys Asp His Pro Trp Arg Asp Met Arg Asn Lys Tyr Gly Ala
    290                 295                 300 ggt aat gcc atg act cct cac tac tct ggt act act tta gac gct caa     960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc    1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa    1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag                1095
Tyr Val Thr Lys Ala Tyr Gly Lys His Asp Lys Lys
        355                 360

<210> SEQ ID NO: 30
<211> LENGTH: 364
<212> TYPE: PRT
<213> ORGANISM: Candida boidinii
```

<400> SEQUENCE: 30

Met Lys Ile Val Leu Val Leu Tyr Asp Ala Gly Lys His Ala Ala Asp
1               5                   10                  15

Glu Glu Lys Leu Tyr Gly Val Thr Glu Asn Lys Leu Gly Ile Ala Asn
                20                  25                  30

Trp Leu Lys Asp Gln Gly His Glu Leu Ile Thr Thr Ser Asp Lys Glu
            35                  40                  45

Gly Glu Thr Ser Glu Leu Asp Lys His Ile Pro Asp Ala Asp Ile Ile
        50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
                100                 105                 110

Leu Glu Val Thr Gly Ser Asn Val Val Ser Val Ala Glu His Val Val
            115                 120                 125

Met Thr Met Leu Val Leu Val Arg Asn Phe Val Pro Ala His Glu Gln
        130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
                180                 185                 190

Tyr Tyr Asp Tyr Gln Ala Leu Pro Lys Glu Ala Glu Lys Val Gly
            195                 200                 205

Ala Arg Arg Val Glu Asn Ile Glu Glu Leu Val Ala Gln Ala Asp Ile
        210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Ser Val Ala Glu Asp Val Ala Ala Leu Glu
                260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO: 31
<211> LENGTH: 1095
<212> TYPE: DNA
<213> ORGANISM: Candida boidinii
<220> FEATURE:
<221> NAME/KEY: CDS

<222> LOCATION: (1)..(1092)

<400> SEQUENCE: 31

```
atg aag att gtc tta gtt ctt tat gat gct ggt aag cac gct gct gat       48
Met Lys Ile Val Leu Val Leu Tyr Asp Ala Gly Lys His Ala Ala Asp
  1               5                  10                  15 gaa gaa aaa tta tat ggt tgt act gaa aat aaa tta ggt att gcc aat       96
Glu Glu Lys Leu Tyr Gly Cys Thr Glu Asn Lys Leu Gly Ile Ala Asn
             20                  25                  30 tgg tta aaa gat caa ggt cat gaa cta att act act tct gat aaa gaa      144
Trp Leu Lys Asp Gln Gly His Glu Leu Ile Thr Thr Ser Asp Lys Glu
         35                  40                  45 ggt gaa aca agc gaa ttg gat aaa cat atc cca gat gct gat att atc      192
Gly Glu Thr Ser Glu Leu Asp Lys His Ile Pro Asp Ala Asp Ile Ile
     50                  55                  60 atc acc act cct ttc cat cct gct tat atc act aag gaa aga ctt gac      240
Ile Thr Thr Pro Phe His Pro Ala Tyr Ile Thr Lys Glu Arg Leu Asp
 65                  70                  75                  80 aag gct aag aac tta aaa tta gtc gtt gtc gct ggt gtt ggt tct gat      288
Lys Ala Lys Asn Leu Lys Leu Val Val Val Ala Gly Val Gly Ser Asp
                 85                  90                  95 cac att gat tta gat tat att aat caa aca ggt aag aaa atc tca gtc      336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc      384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa      432
Met Thr Met Leu Val Leu Val Arg Asn Phe Val Pro Ala His Glu Gln
    130                 135                 140 att att aac cac gat tgg gag gtt gct gct atc gct aag gat gct tac      480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt      528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta      576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt      624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc      672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat      720
Val Thr Val Asn Ala Pro Leu His Ala Gly Thr Lys Gly Leu Ile Asn
225                 230                 235                 240 aag gaa tta tta tct aaa ttt aaa aaa ggt gct tgg tta gtc aat acc      768
Lys Glu Leu Leu Ser Lys Phe Lys Lys Gly Ala Trp Leu Val Asn Thr
                245                 250                 255 gca aga ggt gct att tgt gtt gct gaa gat gtt gca gca gct tta gaa      816
Ala Arg Gly Ala Ile Cys Val Ala Glu Asp Val Ala Ala Ala Leu Glu
            260                 265                 270 tct ggt caa tta aga ggt tac ggt ggt gat gtt tgg ttc cca caa cca      864
Ser Gly Gln Leu Arg Gly Tyr Gly Gly Asp Val Trp Phe Pro Gln Pro
        275                 280                 285 gct cca aag gat cac cca tgg aga gat atg aga aat aaa tat ggt gct      912
Ala Pro Lys Asp His Pro Trp Arg Asp Met Arg Asn Lys Tyr Gly Ala
    290                 295                 300
```

```
ggt aat gcc atg act cct cac tac tct ggt act act tta gac gct caa        960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc       1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggg gaa       1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa tag                   1095
Tyr Val Thr Lys Ala Tyr Gly Lys His Asp Lys Lys
                355                 360
```

<210> SEQ ID NO: 32
<211> LENGTH: 364
<212> TYPE: PRT
<213> ORGANISM: Candida boidinii

<400> SEQUENCE: 32

```
Met Lys Ile Val Leu Val Leu Tyr Asp Ala Gly Lys His Ala Ala Asp
  1               5                  10                  15

Glu Glu Lys Leu Tyr Gly Cys Thr Glu Asn Lys Leu Gly Ile Ala Asn
                 20                  25                  30

Trp Leu Lys Asp Gln Gly His Glu Leu Ile Thr Thr Ser Asp Lys Glu
             35                  40                  45

Gly Glu Thr Ser Glu Leu Asp Lys His Ile Pro Asp Ala Asp Ile Ile
         50                  55                  60

Ile Thr Thr Pro Phe His Pro Ala Tyr Ile Thr Lys Glu Arg Leu Asp
 65                  70                  75                  80

Lys Ala Lys Asn Leu Lys Leu Val Val Val Ala Gly Val Gly Ser Asp
                 85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Leu Glu
            260                 265                 270

Ser Gly Gln Leu Arg Gly Tyr Gly Gly Asp Val Trp Phe Pro Gln Pro
        275                 280                 285
```

```
Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360
```

```
<210> SEQ ID NO: 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
ttttcagtag aaccatataa                                              20

<210> SEQ ID NO: 34
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 34
tatatggttc tactgaaaat                                              20

<210> SEQ ID NO: 35
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 35
cgcgcgtttc ggtgatgacg                                              20

<210> SEQ ID NO: 36
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 36
ctgcagttat ttcttatcgt gtttaccgta                                   30

<210> SEQ ID NO: 37
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 37
gaattcatga agattgtctt agttctttat                                   30
```